(12) United States Patent
Chen et al.

(10) Patent No.: US 6,368,591 B2
(45) Date of Patent: *Apr. 9, 2002

(54) BENEFICIAL MICROBE COMPOSITION, NEW PROTECTIVE MATERIALS FOR THE MICROBES, METHOD TO PREPARE THE SAME AND USES THEREOF

(75) Inventors: Bin Hua Chen; Yi Qiang Yao, both of Shanghai (CN)

(73) Assignee: Shanghai SINE Pharmaceutical Corporation Ltd., Shanghai (CN)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/079,936

(22) Filed: May 15, 1998

(51) Int. Cl.⁷ .............................. A01N 63/00; C12N 1/00
(52) U.S. Cl. ................ 424/93.45; 424/93.4; 424/93.44; 435/252.4; 435/252.9; 435/853; 435/854; 435/885
(58) Field of Search .............................. 424/93.3, 93.45, 424/53.45, 53.4, 53.44; 435/252.4, 252.5, 853, 854, 885

(56) References Cited

U.S. PATENT DOCUMENTS

| 4,806,368 A | | 2/1989 | Reddy | 426/61 |
| 5,085,874 A | * | 2/1992 | Jungvid | 426/41 |
| 5,143,845 A | | 9/1992 | Masuda | 435/252.4 |
| 5,501,857 A | | 3/1996 | Zimmer | 424/438 |
| 5,716,615 A | * | 2/1998 | Cavaliere Vesely et al. | 424/93.4 |

FOREIGN PATENT DOCUMENTS

| FR | 2 479 689 | | 10/1981 |
| JP | 35-10900 | | 8/1970 |
| JP | 57-212122 | | 12/1982 |
| JP | 60-188060 | | 9/1985 |
| JP | 61035759 | * | 2/1986 |
| JP | 63-251080 | | 10/1988 |
| JP | 406038795 | * | 2/1994 |

OTHER PUBLICATIONS

ATCC Catalogue. ATCC Bacteria and Bacteriophages. 19th Edition. 1996. pp. 136 and 346.*
Vitamin Research Products, Inc. Beneficial Bacteria & FOS. VRP's Nutritional News Aug. 31, 1994.

* cited by examiner

*Primary Examiner*—Sandra E. Saucier
*Assistant Examiner*—Vera Afremova
(74) *Attorney, Agent, or Firm*—Albert Wai-Kit Chan; Mark Elkins

(57) ABSTRACT

This invention provides a microbe composition comprising three viable and beneficial lactic acid producing bacteria of new strains: *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005). This invention also provides the materials to protect the viability of the lactic acid producing bacteria in lyophilized form and the method to prepare the composition. Finally, this invention provides various uses of the composition.

12 Claims, No Drawings

BENEFICIAL MICROBE COMPOSITION, NEW PROTECTIVE MATERIALS FOR THE MICROBES, METHOD TO PREPARE THE SAME AND USES THEREOF

Throughout this application, various publications are referenced and full citations for these publications may be found in the reference at the end of the specification preceding the claims. The disclosures of these publications are hereby incorporated by reference into this application in order to more fully describe the state of the art as known to the skilled therein as of the date of the invention described and claimed herein.

BACKGROUND OF THE INVENTION

It is well known that inside the gastrointestinal tract of each human being resides a microbial flora, which is a rich ecosystem of enormous complexity containing trillions of bacteria divided into more than 400 species. In addition to the normal microbial flora (resident micro flora) already established in the gastrointestinal tract, bacteria are introduced into human body everyday as a normal part of food (transient micro flora) or as contaminants (accidental micro flora).

The bacteria in human gastrointestinal tract can be divided into two groups—the probiotics and the pathogens. The probiotics are beneficial since they participate in a wide variety of positive and health promoting activities in human physiology. The pathogens are harmful as they cause diseases. Normally the probiotics prevail and predominate. The microscopic interplay between probiotics and pathogens and the balance between the beneficial and the harmful microorganisms are essential for a properly functioning digestive tract, which is in turn crucial to the optimal health of a human being. The number and efficiency of probiotics decline as people age or decrease in health.

The major benefits probiotics render to human beings are as follows:

The presence and adherence of probiotics, especially many lactic acid producing bacteria to the mucous membrane of the intestine from ileo-caecal region downward constitute a formidable natural biologic barrier for many pathogenic bacteria. The probiotics compete with disease-causing bacteria for villi attachment sites and nutrients. In addition, many kinds of acid produced by probiotics, such as lactic acid, acetic acid and benzoic acid, create an acidic environment unfriendly to harmful bacteria, viruses and yeasts.(1) The metabolic by-products of many probiotics, called bacteriocins, such as hydrogen peroxide, lactocidin, acidophilin and bulgarican, also manifest antibiotic properties and inhibit the growth of a wide spectrum of pathogens and/or potential pathogens, such as Escherichia (particularly *E. coli*), Klebsiella, Enterobacter, Pseudomonas, Salmonella, Serratia and Bacteroides.(2)

The metabolic products of probiotics provide many useful enzymes and volatile or non-volatile fatty acids to help digestion and absorption of certain minerals, such as phosphorus, calcium and iron.(3)

Probiotics contribute to a shorter intestinal transit time as well. This effect may be useful in some cases of constipation, particularly for the elder people.

Many resident enteric probiotics also produce certain important vitamins of B complex such as niacin (B3), pyridoxine (B6), folic acid and biotin for the needs of the host human being.

The lactic acid producing bacteria confer significant protection for human beings through various immune mechanisms, that include interactions between the microbes and the host as well as interactions among microbes.(4)

Probiotics also have powerful anti-carcinogenic features, that are active against certain tumors.(5) Epidemiological reports indicate an inverse relationship between colon cancer risk and consumption of fermented milks containing certain probiotics.(6) *Bifidobacterium bifidum* and *Lactobacillus acidophilus* have been shown in human clinical studies as being able to reduce the levels of some colonic enzymes (β-glucuronidase, nitroreductase, azoreductase and glycoholic acid hydrolase), that are implicated in the conversion of procarcinogens to carcinogens such as nitrosamine or secondary bile salts.(7)

Probiotics play such an integral part in the health of human being that some leading researchers in Europe claim that as much as 80% of all degenerative diseases result from an imbalance in the intestinal flora.

Probiotics, especially certain lactic acid producing bacteria have been used to ferment food for at least 4,000 years. Without understanding the scientific basis, people used these bacteria to produce cultured food with improved preservation and different flavors and textures from the original food. A wide variety of food including sausage, ham, wine, cider, beer, sauerkraut, olives and pickles all contain beneficial bacteria. Lactic acid producing bacteria are also used for many fermented milk products from all over the world, including yogurt, cheese, butter, buttermilk, kefir and koumiss.

The health benefits associated with probiotics were first observed by Nobel prize winner Elie Metchnikoff in the early 1900's when he hypothesized that lactobacilli were important in the intestinal flora for the health and longevity of human beings.(8) At about the same time, Tissier also showed that Bifidobacteria were the predominant flora in breast-fed infants and speculated that infant diarrhea could be treated by giving large doses of Bifidobacteria orally.(9) Since then, much research has been performed in an attempt to elucidate the mechanism of action of probiotics in the intestines on good health.

Scientific interest in probiotics has increased notably in past decades as the widespread use of antibiotics such as penicillin to suppress infection also brought many side effects. Antibiotics eliminate both harmful and beneficial bacteria at the same time and disturb the balance of normal bacteria flora in human body. Patients after long period or large amount use of antibiotics are often extremely susceptible to the secondary infection. In addition, many pathogens and/or potential pathogens have acquired immunity to antibiotics over the years. Researchers all over the world are looking for a method which can suppress disease causing bacteria without disturbing the normal microbial flora in the human body. Since more and more researches have shown that probiotics have the property to inhibit the growth of pathogens and/or potential pathogens and their levels can fluctuate and be manipulated, attempts have been made to increase the number and activity of these bacteria by consuming live cultures of selected species of bacteria in milk, yogurt, or pure cultures in powder, tablet or capsule form.

In China, strain selection on certain bacteria with health benefits was undertaken in the early 1980's when a group of scientists at the Institute of Epidemiology and Microbiology of the Chinese Preventive Medical Academy succeeded in isolating various anaerobes from the feces of 1–5 years old healthy children. They compared the number of beneficial microbes in the feces of healthy people with that of those suffering from diarrhoeal conditions, finding that Bifidobacteria together with other Gram positive non-sporing rods and residential Gram negative bacteria such as Bacteroides were greatly reduced in number in diarrhoeal patients as compared with the normal ones.(10) Realizing the significance of their findings, these scientists next performed experiments in gnotobiotic gineapigs with the *Bifidobacterium bifidum* and a combination of *Bifidobacterium bifidum, Lactobacillus acidophilus* and *Sterptococcus faecalis*. Challenged with a virulent strain of *Shigella flexneri* 2a, the researchers found that animals implanted and colonized with *Bifidobacterium bifidum* exhibited marked resistance to Shigella infection whereas the controls succumbed. They also discovered that *Bifidobacterium bifidum, Lactobacillus acidophilus* and *Streptococcus faecalis*, when used together, performed a synergistic action in killing *Shigella sonnei*.(11) Another study, using gnotocavy dysentery model test, also showed that the protection of *Bifidobacterium bifidum* to animal (50%) was lower than that of the three bacteria combined (75%).(12)

In the past three decades, although much progress has been made in the field of probiotic research, problems exist. First of all, although some health benefits of probiotics are now well documented, not all of the varied hypotheses have been substantiated. The problems are in part related to the fact that most health effects of probiotics are species, even strain dependent and specific, and varying results may occur when using different strains of the same species or even different preparations of the same strain. There is also a large variability in the physiology of individuals and large populations must be studied to provide valid results. In addition, many bacteria species, such as *Lactobacillus acidophilus*, are not viable for a great length of storage time. The 1983 University of Wyoming survey conducted by Brennan et. al. proved that the viability claims of various manufactures did not hold true with their products. Also, a majority of the probiotics get rapidly inactivated in the human upper gastrointestinal tract, where the pH is close to 2.0 to 2.9, even before they reach the lower intestines.(13) For example, China Pat. No. CN 1,103,584 describes an oral solution comprising three lactic acid producing bacteria consisting of *Bifidobacterium bifidum, Lactobacillus acidophilus* and *Sterptococcus faecalis*. This oral solution is problematic since its stability and viable ratio of microbes are low and it is difficult to store.

Notable efforts have been made since the 1980's on selection of probiotic strains with proven therapeutic properties and survival ability. U.S. Pat. No. 5,143,845 discloses a symbiotic mixture containing three kinds of bacteria as effective ingredients that consist essentially of lactic acid producing bacteria such as *Sterptococcus faecalis*, saccarificating bacteria such as *Bacillus mesentericus* and butyric acid producing bacteria such as *Clostridium butyricum*. The patent also provides an unique method for culturing these three kinds of bacteria, that comprises propagating saccarificating bacteria in a culture medium containing a protein as the source of nitrogen and a carbohydrate as the source of carbon. After filtering the culture fluid to remove the saccarificating bacteria, the filtrate is introduced to a fresh culture medium, in which lactic acid producing bacteria are cultured under aerobic conditions. Then both the lactic acid producing bacteria and the butyric acid producing bacteria are propagated under anaerobic conditions in the fresh medium containing the culture fluid from the culture of the lactic acid producing bacteria. The lactic acid producing bacteria and the butyric acid producing bacteria are segmented from the culture medium after the spore formation of butyric acid producing bacteria.

U.S. Pat. No. 4,806,368 describes a nutritional supplement tablet using a lyophilized preparation of *Lactobacillus acidophilus* and/or *Bifidobacterium bifidus, Leuconostoc citrovorum* and *Propionibacterium shermanii*. To enhance the viability of the lyophilized bacterial preparations in the tablet, the reducing compounds such as amino acid L-cystine are included. To protect the beneficial bacterial population in the human stomach and intestinal tract, the minerals such as calcium carbonate and magnesium oxide are incorporated in the formula. The Lecithin is employed as a natural lubricant to aid the tablet preparation. The milk derived ingredients such as acid whey powder, whey protein concentrate and enzyme digested casein are used as bacterial growth enhancers. Also, the acid whey supplies bioavailable minerals, simple and complex carbohydrate substrates and lactates to the bacterial growth in the intestinal tract. Further, autolyzed yeast extract is incorporated as a stimulant to the beneficial bacteria in the gastrointestinal tract, a major source of B-vitamins and a supplier of most of the major and minor trace minerals. Although vitamins A, C, D and E are included in the formula primarily as nutritional supplements, vitamins C and E also protect the bacterial cells in the tablets together with L-cystine due to their antioxidation properties. Similarly, although the diet fiber is used in the tablets, with a major proportion, mainly as a dietary supplement, the fiber, after reconstitution, also has an exceptionally protective and stimulatory effect on the growth of the probiotics in the presence of neutralizing calcium and magnesium salts.

Another composition entitled BioPRO® provided by Vitamin Research Products, Inc. located at 3579 Hwy. 50 East, Carson City, Nev. 89701 contains three species of bacteria: *Lactobacillus acidophilus* DDS-1 and *Bifidobacterium bifidum* and *streptococcus faceum*, all developed at the University of Nebraska. BioPRO® takes the formulation of capsule, each containing a minimum of one billion active bacteria. In addition to the bacteria, Lactobacillus Growth Factor and Fructooligosaccharides are also included in the composition to enhance the potency of BioPRO® Fructooligosaccharides are a simple class of natural carbohydrates, that exist in small quantities in people's daily diet. Fructooligosaccharides are non-digestible, S short-chain fructose polymers that are utilized almost exclusively by the Bifidobacteria and Lactobacteria in intestinal tract of a human being. While Fructooligosaccharides can be used to enhance the growth of beneficial bacteria, harmful bacteria such as Clostridium, Salmonella and *E.Coli* can not get any benefits of Fructooligosaccharides. Human clinical studies have demonstrated the stimulating effect of Fructooligosaccharides on beneficial bacteria. At the clinical trials, the number of beneficial bacteria increased up to a 10-fold after Fructooligosaccharides supplementation of 1 to 4 grams.

U.S. Pat. No. 5,501,857 discloses a nutritional and dietary composition which combines certain incompatible substances such as nutrient supplements and viable direct-fed microbials in the form of a double capsule, which includes an inner capsule and an outer capsule. The outer capsule is spaced apart from and encloses the inner capsule. The inner capsule includes a dissolvable gelatin shell and a first substance. The outer capsule includes a dissolvable gelatin shell and a second substance. One of the substances is viable gastrointestinal microorganisms and the other substance is a nutritional supplement having the property of diminishing viability of the microorganisms.

The microorganisms are selected from the group consisting of gastrointestinal bacteria, live cell yeasts, fungi and a combination thereof, wherein the bacteria are one or more of the genus Lactobacillus, Streptococcus, Pediococcus, Bifidobacterium or Propionibacterium; the live cell yeast is the genus Saccharomyces; and the fungus is the genus Aspergillus. The nutritional supplement is selected from the group consisting of vitamins, minerals and a combination thereof, wherein the vitamins include one or more of vitamin A, vitamin D, vitamin E, Vitamin B12, riboflavin, niacin, pantothenic acid, thiamine, choline, folic acid, biotin, vitamin K and vitamin C, and the minerals includes one or more of cobalt, copper, iron, manganese, zinc and selenium. The composition is shelf stable and allows substantially greater viability of the microbials by using this capsule-in-a-capsule structure. U.S. Pat. No. 5,501,857 demonstrates that the bacterial survival rate with this capsule-in-a-capsule structure after six months of preparation is nearly 500 times that of an admixture of the bacteria and nutrient supplements.

SUMMARY OF THE INVENTION

It is the object of the present invention to provide a microbe composition which: (1) exerts a control mechanism for the micro ecological balance between enteric microbes and their human host; (2) is antagonistic to pathogens and/or potential pathogens such as Salmonella, Shigella, *E. coli* and *V. cholerae*, especially when the pathogens and/or potential pathogens are resistant to various antibiotics; (3) is effective in treating various kinds and degrees of diarrhea; (4) stimulates peristaltic movement of the intestinal tract which not only prevents toxic microbial colonization and eliminates noxious microbial products but also alleviates constipation; (5) enhances immunologic function of the human host; (6) is effective in decreasing the levels of endotoxin and abnormally elevated cytokine IL-6 in the blood of the human host; (7) is effective in improving and enhancing liver function; (8) is effective in treating acute and chronic hepatitis in active stage especially when it is accompanied with endotoximia; (9) is effective in alleviating liver cirrhosis; (10) is non-toxic and has no side effects and (11) is stable, convenient to store and use.

It is also an object of the present invention to protect and enhance the viability of the beneficial bacteria in the microbe composition in lyophilized form over a long period of time.

It is another object of the present invention to provide a method to prepare the microbe composition.

The present invention relates generally to a microbe composition comprising beneficial microorganisms of new strains and particularly to a symbiotic mixture of three lactic acid producing bacteria consisting of *Bifidobacterium longum* 6-1, *Lactobacillus acidophilus* YIT 2004 and *Sterptococcus faecalis* YIT 0027. The invention also concerns new materials to protect the viability of the bacteria in lyophilized form. In a ddition, the invention pertains to a method for culturing the microorganisms and preparing the microbe composition. The composition helps replenish the intestine with normal biological bacteria and adjust the balance of enteric bacterial species. It is also used in the treatment of acute and chronic diarrhea, abdominal distention and constipation. In addition, the composition inhibits the growth of pathogens and/or potential pathogens in the intestines, promotes the decomposition and absorption of nutritions, provides essential vitamins, enhances the body immune system and reduces the absorption of intestinal toxin to ease the burden of the liver. The composition is useful for both human beings and animals. Accordingly, the present invention will be described in detail with respect to such fields of endeavor; however, those skilled in the art will appreciate that such description of the invention is meant to be exemplary only and should not be viewed as limitative of the full scope thereof.

DETAILED DESCRIPTION OF THE INVENTION

This invention provides a microbe composition comprising the bacteria *Bifidobacterium longum* 6-1.

*Bifidobacterium longum* 6-1 is an anaerobic bacterium which, grows under anaerobic or slight aerobic conditions. The optimal growth temperature for *Bifidobacterium longum* 6-1 is 37–380C and the optimal pH value is 6.5–7.4. The strain of *Bifidobacterium Longum* 6-1 of this invention was developed and provided by the Institute of Epidemiology and Microbiology of the Chinese Preventive Medical-Academy.

The method for culturing and identifying *Bifidobacterium longum* 6-1 is as follows: dissolving 0.5 g. fresh feces selected from healthy children (1–5 years old) with 4.5 ml. PBS solution; diluting the solution with PBS solution further to a suitable concentration and plating out on the BL medium; after 72 hours of culture at the temperature of 37° C. under anaerobic conditions, *Bifidobacterium longum* 6-7. forms round, a bit of protrusive, milky white, smooth and adherent colonies from 0.5 to 2 mm; Gram's stain of *Bifidobacterium longum* 6-1 is positive but inhomogeneous; the strain has neither spore nor capsule nor flagellum; the mycelia are straight or curved or Y-, V- and stick type; selecting typical colony for sterile culture and aerobic test; the strain of *Bifidobacterium longum* 6-1 is selected and tested under microscope together with test of physiological and biochemical reaction and analysis of metabolites; the strain is identified as *Bifidobacterium longum* 6-1, which is in agreement with some descriptions made by Buchanan B L et al. in Bergeys Manual of Determinative Bacteriology Eighth ed. (1977).

The following table compares the physicochemical characteristics of *Bifidobacterium longum* and *Bifidobacterium longum* 6-1.

TABLE 1

Comparison of Physicochemical Characteristics of *Bifidobacterium longum* and *Bifidobacterium longum* 6-1

| Strain Characteristics | B. longum | B. Longum 6-1 |
|---|---|---|
| Gram's Stain | $G^+$ | $G^+$ |
| Motive Force | – | – |
| Enzyme Test | – | – |
| Methylene Blue Milk Test | – | – |
| Milk Coagulation | + | + |
| 6.5% NaCl Meat Extract | – | – |
| Gelatinum Liquefaction Test | – | – |
| Carbohydrate Fermentation Test | | |
| Glucose | + | + |
| Lactose | + | + |
| Maltose | – | + |
| Gossypose | – | + |
| Sucrose | – | – |
| Sorbic Alcohol | – | – |
| Mannose | – | – |
| 45° C. Anaerobic Culture | – | – |
| 45° C. Aerobic Culture | – | – |

*Bifidobacterium*(14) *longum* is by far the most researched species known as being able to produce natural antibiotics, including anti-virus compounds. Staying mainly inside the colon and rectum (lower intestine), *Bifidobacterium longum* is effective in killing and/or inhibiting bacteria, such as *Escherichia coli, S. aureus* and shigella, and some yeasts and viruses that may cause certain diseases. *Bifidobacterium longum* helps not only to detoxify bile from which they recycle oestrogen in women but also to prevent potential toxicity from nitrites coming with food. Manufacturing various IB vitamins, *Bifidobacteri@m longum* has also been shown in human clinical studies as being able to reduce the levels of some colonic enzymes (β-glucuronidase, nitroreductase, azoreductase and glycoholic acid hydrolase), which are implicated in the conversion of procarcinogens to carcinogens such as nitrosamine or secondary bile salts.(15)

This invention provides the isolated bacteria *Bifidobacterium longum* 6-1. This bacteria was deposited on Feb. 23, 1998 with the international deposit agency in the People's Republic of China, China Center for Type Culture Collection, located on the campus of Wuhan University, Wuhan 430072, P. R. China, with the telephone No. 86-027-7882712, Fax No. 86-27-7883833, under the provisions of the Budapest Treaty for the International Recognition of the Deposit of Microorganism for the Purposes of Patent Procedure. The viability of the culture was tested on Feb. 26, 1998. The culture was viable on that day. *Bifidobacterium longum* 6-1 was accorded China Center for Type Culture Colletion (CCTCC) Number M 98003.

This invention provides a microbe composition comprising the bacteria *Lactobacillus acidophilus* YIT 2004.

*Lactobacillus acidophilus* YIT 2004 is a facultative anaerobe bacterium. The optimal growth temperature for *Lactobacillus acidophilus* YIT 2004 is 37–400C, but the bacteria can also grow at the temperature of 45° C. The optimal pH value is 5.5–6.5. After 48 hours of culture under aerobic condition, *Lactobacillus acidophilus* YIT 2004 forms round, a bit of protrusive, milky white and smooth colonies on the BL plat. The diameter of the colonies is about 1 mm. Gram's stain of *Lactobacillus acidophilus* YIT 2004 is positive. The strain has neither spore, nor capsule nor flagellum. The mycelia are short stick-like or ball stick-like with blunt round at two site of stick-like mycelia and are arranged in single or twin form.

The strain of *Lactobacillus acidophilus* YIT 2004 of this invention was provided by Japan Gifu pharmaceutical University.

*Lactobacillus acidophilus* is carefully selected for use in this invention. Extensive literature backs up the health benefits of *Lactobacillus acidophilus* for human being. Consuming sugars and producing lactic acid, *Lactobacillus acidophilus* inhabits primarily in the stomach and intestinum ileum. In vitro studies have demonstrated antagonistic activity of *Lactobacillus acidophilus* against a variety of pathogens and/or potential pathogens, such as *Helicobacter pylori*,(16) *Yersini pseudotuberculosis, Salmonella typhimurium*(17) and *Shigella sonnei*.(18) Animal studies have further shown prevention of infections produced by *Escherichia coli, Listeria monocytogenes*(19) and *Shigella sonnei*.(20) These results have been attributed to certain specific compounds produced by *Lactobacillus acidophilus* that include certain antimicrobial compounds such as organic acids and hydrogen peroxide, antibiotic-like compounds such as lactocidin, acidophilin and bulgarican, (21) and bacteriocins (proteins or protein complexes that exert antibacterial activity against closely related species(22) such as lactacin-B and lactacin-F).(23) As early as 1950, *acidophilus* had been recognized by the U.S. government as a drug, when it was found equally effective as neomycin sulfate for *E. coli* infections.(24) *Lactobacillus acidophilus* also produces certain enzymes such as protease that digest proteins and lipase, that digest fats. In addition, the bacteria have the effect of shortening intestinal transit time, improving immune response and reducing serum cholesterol levels. Since the bacteria break down lactose (milk sugar) into more easily digestible simple sugars, *Lactobacillus acidophilus* can treat lactose intolerance. The bacteria can also help to decrease carcinogen production since they are able to reduce the level of several colonic enzymes (0-glucuronidase, nitroreductase, azoreductase and glycoholic acid hydrolase) that are implicated in the conversion of procarcinogens to carcinogens such as nitrosamine or secondary bile salts.(25) In vitro studies have as well shown decreased mutagenic activity of heterocyclic amines (procarcinogens) in the presence of *Lactobacillus acidophilus*. Direct binding of procarcinogens may be responsible for this effect.(26)

This invention provides the isolated bacteria *Lactobacillus acidophilus* YIT 2004. This bacteria was deposited on Feb. 23, 1998 with the international deposit agency in the People's Republic of China, China Center for Type Culture Collection, located on the campus of Wuhan University, Wuhan 430072, P. R. China, with the telephone No. 86-027-7882712, Fax No. 86-27-7883833, under the provisions of the Budapest Treaty for t he International Recognition of the Deposit of Microorganism for the Purposes of Patent Procedure. The viability of the culture was tested on Feb. 26, 1998. The culture was viable on that day. *Lactobacillus acidophilus* YIT 2004 was accorded China Center for Type Culture Colletion (CCTCC) Number M98004.

This invention provides a microbe composition comprising the bacteria *Sterptococcus faecalis* YIT 0027.

*Sterptococcus faecalis* YIT 0027 is an facultative anaerobe bacterium. The optimal growth temperature for *Sterptococcus faecalis* YIT 0027 is 37–40° C., but the bacteria can also grow well at the temperature of 45° C. The optimal pH value is 6.5–7.6. After 24 hours of culture under aerobic condition, *Sterptococcus faecalis* YIT 0027 forms round, a bit of protrusive, gray white and smooth colonies on the BL plat. Gram's stain of *Sterptococcus faecalis* YIT 0027 is positive. The strain ha s neither spore, capsule, nor flagellum. The mycelia are egg round, arranged in twin or short chain form. The strain of *Sterptococcus faecalis* YIT 0027 of this invention was also provided by Japan Gifu pharmaceutical University.

This invention provides the isolated bacteria *Sterptococcus faecalis* YIT 0027. This bacteria was deposited on Feb. 23, 1998 with the international deposit agency in the People's Republic of China, China Center for Type Culture Collection, located on the campus of Wuhan University, Waliaci 430072, P. R. China, with the telephone No. 86-027-7882712, Pax No. 86-27-7883833, under the provisions of the Budapest Treaty for the International Recognition of the Deposit of Microorganism for the Purposes of Patent Procedure. The viability of the culture was tested on Feb. 26, 1998. The culture was viable on that day. *Sterptococcus faecalis* YIT 0027 was accorded China Center for Type Culture Collection (CCTCC) Number M 98005.

This invention provides a microbe composition comprising the bacteria *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005).

This invention provides a microbe composition comprising the bacteria *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005) with a content ratio as 1-5:1-5:1-5.

The content ratios used herein are the respective numbers of colony-forming units per gram (CFU/G) for each microbe.

This invention provides a microbe composition comprising the bacteria *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005) with a content ratio as 5:5:3.

This invention provides a microbe composition comprising the bacteria *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005) with a content ratio as 5:3:3.

This invention provides a microbe composition comprising the bacteria *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005) with a content ratio as 5:3:5.

This invention provides a microbe composition comprising the bacteria *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005) with a content ratio as 5:5:1.

This invention provides a microbe composition comprising the bacteria *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005) with a content ratio as 5:3:1.

All three bacterium strains selected for this microbe composition have been shown as being able to survive human stomach acidity as well as propagate at physiological levels of bile salts and adhere to the intestinal epithelial cells.

The combination of three bacterium strains has an advantage over single bacterium strain preparation since each of the three bacterium strains has its characteristics and specialized roles and is synergetic with each other. Each bacterium strain will differentiate itself in the intestinal tract by finding its most favorable environment to survive the intense temperature and high concentrations of bile salts in the intestinal tract. As a result, this combination is able to control pathogenic bacteria in the entire human intestine instead of only a part of it. This combination also produces an enhanced inhibitory capacity than that of a single bacterium preparation, that brings the beneficial effects of three bacterium strains into fast and steady play.

This invention provides a microbe composition comprising the bacteria *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005) in the form of lyophilized powder. By the term of "lyophilized," it is intended to include substantially any techniques or variations for preserving viable bacteria in a dry or powered form, such that the bacteria can be incorporated into the formulation of a pill, capsule, tablet, granule or suspension.

This invention provides the above microbe compositions further comprising a protective medium wherein said protective medium is 10–20% dried skim milk, 10–20% lactulose, 0.01–0.2% sodium vitamin C, 0.01–2% sodium glutamate, 0.01–2% vitamin E, 6–20% of β-cyclodextrin and 6–20% starch.

This invention provides the above microbe compositions wherein said protective medium is 10–20% dried skim milk, 10–20% lactulose, 0.01–0.2% sodium vitamin C, 0.01–2% sodium glutamate, 0.01–2% vitamin E and 6–20% starch.

This invention provides the above microbe compositions wherein said protective medium is 10–20% lactulose, 0.01–0.2% sodium vitamin C, 0.01–2% vitamin E and 6–20% starch.

This invention provides a microbe composition comprising the bacteria *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005) and a protective medium.

This invention provides a microbe composition comprising the bacteria *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005) and a protective medium with a content ratio between bacteria and protective medium as 0.01–99.99% to 99.99–0.01%.

The following tables show the stability of lyophilized powder of *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005). All temperatures are expressed in degrees Celsius. Microbial viability is expressed in colony-forming units per gram of source material (CFU/G).

TABLE 2

Stability of Lyophilized Powder of *Bifidobacterium longum* 6-1 (CCTCC Number M 98003) (Storage temperature 2–8° C.)

| Batch No. | Storage Time | Viable Bacteria CFU/G (Original) | Viable Bacteria, CFU/G (Test results) | Change |
|---|---|---|---|---|
| 1 | 1 Year | $3.5 \times 10^9$ | $1.0 \times 10^{10}$ | No Change |
| 2 | 6 Month | $2.2 \times 10^9$ | $2.7 \times 10^9$ | No Change |
| 3 | 6 Month | $1.7 \times 10^{10}$ | $2.7 \times 10^9$ | Lower $1.0 \times 10^1$ |
| 4 | 1 Year | $3.0 \times 10^7$ | $1.0 \times 10^7$ | No Change |
| 5 | 1 Year | $1.0 \times 10^7$ | $1.1 \times 10^7$ | No Change |
| 6 | 1 Year | $3.0 \times 10^7$ | $2.4 \times 10^6$ | Lower $1.0 \times 10^1$ |

TABLE 3

Stability of Lyophilized Powder of *Lactobacillus acidophilus* YIT 2004 (CCTCC Number M 98004) (Storage temperature 2–80° C.)

| Batch No. | Storage Time | Viable Bacteria CFU/G (Original) | Viable Bacteria, CFU/G (Test results) | Change |
|---|---|---|---|---|
| 1 | 1 Year | $4.6 \times 10^9$ | $1.0 \times 10^8$ | Lower $1.0 \times 10^1$ |
| 2 | 1 Year | $3.0 \times 10^9$ | $1.7 \times 10^8$ | Lower $1.0 \times 10^1$ |
| 3 | 1 Year | $1.7 \times 10^9$ | $5.0 \times 10^7$ | Lower $1.0 \times 10^1$ |
| 4 | 10 Months | $3.0 \times 10^9$ | $2.0 \times 10^8$ | Lower $1.0 \times 10^1$ |
| 5 | 6 Months | $1.0 \times 10^{11}$ | $8.0 \times 10^{10}$ | Lower $1.0 \times 10^1$ |
| 6 | 6 Months | $2.0 \times 10^{10}$ | $1.0 \times 10^{10}$ | No Change |

TABLE 4

Stability of Lyophilized Power of *Streptococcus faecalis* YIT 0027(CCTCC Number M 98005) (Storage temperature 2–8° C.)

| Batch No. | Storage Time | Viable Bacteria CFU/G (Original) | Viable Bacteria, CFU/G (Test results) | Change |
|---|---|---|---|---|
| 1 | 1 Year | $3.0 \times 10^{10}$ | $3.0 \times 10^9$ | Lower $1.0 \times 10^1$ |
| 2 | 1 Year | $3.0 \times 10^{10}$ | $2.8 \times 10^9$ | Lower $1.0 \times 10^1$ |
| 3 | 1 Year | $2.0 \times 10^{10}$ | $1.5 \times 10^9$ | Lower $1.0 \times 10^1$ |
| 4 | 11 Months | $6.0 \times 10^9$ | $3.5 \times 10^8$ | Lower $1.0 \times 10^1$ |
| 5 | 6 Months | $3.0 \times 10^{10}$ | $5.0 \times 10^9$ | Lower $1.0 \times 10^1$ |
| 6 | 6 Months | $3.0 \times 10^{10}$ | $2.2 \times 10^{10}$ | No Change |

The following tables show the stability of the microbe composition comprising *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005) in the formulation of capsule. The microbe compositions in table 5 and 6 were prepared with zymotic fluid comprising skim milk, glucose, ammonia sulfate, monopotassium phosphate, dipotassium hydrogen phosphate and calcium carbonate and with protective materials comprising skim milk, lactulose, sodium vitamin C and sodium glutamate. The microbe composition in table 7 was prepared with zymotic fluid comprising skim milk, glucose, yeast powder, ammonia sulfate, monopotassium phosphate, dipotassium hydrogen phosphate and calcium carbonate and with protective materials comprising skim milk, lactulose, sodium vitamin C, sodium glutamate, vitamin E, β-cyclodextrin and compressible starch. All temperatures are expressed in degrees Celsius. Microbial viability is expressed in colony-forming units per gram of source material (CFU/G).

TABLE 5

Stability of the microbe composition comprising
*Bifidobacterium longum* 6-1(CCTCC Number M 98003),
*Lactobacillus acidophilus* YIT 2004 (CCTCC Number M 98004)
and *Streptococcus faecalis* YIT 0027 (CCTCC Number M 98005)
in the formulation of capsule after Storage for Six Months
at 25 ± 5° C.

| Batch No. | Viable Bacteria (Original) CFU/G | | | Viable Bacteria (Test Results) CFU/G | | |
|---|---|---|---|---|---|---|
| | B.b | L.a | S.f | B.b | L.a | S.f |
| 1 | $1.0 \times 10^9$ | $8.0 \times 10^7$ | $1.5 \times 10^7$ | $1.0 \times 10^9$ | $2.5 \times 10^7$ | $1.6 \times 10^7$ |
| 2 | $1.0 \times 10^9$ | $8.0 \times 10^7$ | $2.0 \times 10^7$ | $1.0 \times 10^9$ | $3.0 \times 10^7$ | $1.0 \times 10^7$ |
| 3 | $1.0 \times 10^9$ | $6.0 \times 10^7$ | $4.0 \times 10^6$ | $1.0 \times 10^8$ | $3.1 \times 10^7$ | $1.6 \times 10^6$ |
| 4 | $3.0 \times 10^9$ | $2.5 \times 10^7$ | $4.0 \times 10^7$ | $2.0 \times 10^9$ | $1.0 \times 10^7$ | $1.3 \times 10^7$ |
| 5 | $1.5 \times 10^9$ | $2.0 \times 10^8$ | $6.0 \times 10^7$ | $3.0 \times 10^8$ | $3.0 \times 10^7$ | $2.0 \times 10^7$ |
| 6 | $8.0 \times 10^8$ | $8.0 \times 10^7$ | $4.0 \times 10^7$ | $3.0 \times 10^8$ | $2.0 \times 10^7$ | $2.0 \times 10^7$ |

The total viable bacteria is 1.9–6.5 hundred million CFU/g. when produced and 6.7–30 million CFU/g. after storage in refrigerator for one year.

TABLE 6

Stability of the microbe composition comprising
*Bifidobacterium longum* 6-1 (CCTCC Number M 98003),
*Lactobacillus acidophilus* YIT 2004 (CCTCC Number M 98004)
and *Streptococcus faecalis* YIT 0027 (CCTCC Number M 98005)
in the formulation of capsule after Storage for Six Months
at 25° C.

| Batch No. | Viable Bacteria (Original) CFU/G | | | Viable Bacteria (Test Results) CFU/G | | |
|---|---|---|---|---|---|---|
| | B.b | L.a | S.f | B.b | L.a | S.f |
| 1 | $2.5 \times 10^7$ | $2.0 \times 10^8$ | $8.0 \times 10^8$ | $1.4 \times 10^6$ | $3.2 \times 10^7$ | $3.0 \times 10^7$ |
| 2 | $6.0 \times 10^7$ | $1.8 \times 10^7$ | $1.0 \times 10^8$ | $1.4 \times 10^6$ | $1.2 \times 10^6$ | $3.8 \times 10^7$ |
| 3 | $8.0 \times 10^7$ | $3.0 \times 10^7$ | $3.1 \times 10^8$ | $3.1 \times 10^6$ | $1.8 \times 10^7$ | $2.9 \times 10^7$ |
| 4 | $6.3 \times 10^6$ | $1.2 \times 10^8$ | $5.9 \times 10^7$ | $4.8 \times 10^5$ | $1.1 \times 10^7$ | $4.9 \times 10^6$ |
| 5 | $5.9 \times 10^6$ | $1.1 \times 10^8$ | $1.3 \times 10^7$ | $1.25 \times 10^5$ | $3.0 \times 10^7$ | $1.1 \times 10^7$ |
| Average | $3.544 \times 10^7$ | $9.56 \times 10^7$ | $2.564 \times 10^8$ | $1.301 \times 10^6$ | $1.844 \times 10^7$ | $1.141 \times 10^7$ |

TABLE 7

Stability of the microbe composition comprising
*Bifidobacteriuin longum* 6-1 (CCTCC Number M 98003),
*Lactobacillus acidophilus* YIT 2004 (CCTCC Number M 98004)
and *Streptococcus faecalis* YIT 0027 (CCTCC Number M 98005)
in the formulation of capsule after Storage for Six Months
at 25° C.

| Batch No. | Viable Bacteria (Original) CFU/G | | | Viable Bacteria (Test Results) CFU/G | | |
|---|---|---|---|---|---|---|
| | B.b | L.a | S.f | B.b | L.a | S.f |
| 1 | $2.7 \times 10^9$ | $1.9 \times 10^9$ | $3.0 \times 10^{10}$ | $2.3 \times 10^9$ | $1.5 \times 10^9$ | $3.2 \times 10^{10}$ |
| 2 | $6.4 \times 10^9$ | $1.6 \times 10^{10}$ | $1.6 \times 10^{10}$ | $5.4 \times 10^9$ | $8.0 \times 10^9$ | $1.5 \times 10^{10}$ |

TABLE 7-continued

Stability of the microbe composition comprising
Bifidobacteriuin longum 6-1 (CCTCC Number M 98003),
Lactobacillus acidophilus YIT 2004 (CCTCC Number M 98004)
and Streptococcus faecalis YIT 0027 (CCTCC Number M 98005)
in the formulation of capsule after Storage for Six Months
at 25° C.

| Batch | Viable Bacteria (Original) CFU/G | | | Viable Bacteria (Test Results) CFU/G | | |
|---|---|---|---|---|---|---|
| No. | B.b | L.a | S.f | B.b | L.a | S.f |
| 3 | $1.2 \times 10^{10}$ | $8.0 \times 10^{9}$ | $2.0 \times 10^{10}$ | $1.0 \times 10^{10}$ | $7.6 \times 10^{9}$ | $1.9 \times 10^{10}$ |
| 4 | $2.9 \times 10^{10}$ | $6.0 \times 10^{9}$ | $9.0 \times 10^{9}$ | $2.7 \times 10^{10}$ | $3.8 \times 10^{9}$ | $8.0 \times 10^{9}$ |
| 5 | $8.4 \times 10^{9}$ | $1.2 \times 10^{10}$ | $7.8 \times 10^{10}$ | $1.0 \times 10^{10}$ | $1.0 \times 10^{10}$ | $1.0 \times 10^{10}$ |
| Average | $1.17 \times 10^{10}$ | $8.78 \times 10^{9}$ | $3.06 \times 10^{10}$ | $1.094 \times 10^{10}$ | $6.18 \times 10^{9}$ | $1.68 \times 10^{10}$ |

This invention provides a method for preparing a microbe composition comprising steps of: (a) mixing solutions of 3.5–4% dried skim milk, 1% glucose and 3% yeast extract; (b) sterilizing the mixed solution in a autoclave at a temperature of 1210C for 10 minutes, then allowing sterilized medium to cool to 37–380C and transferring the medium to three fermentation tanks; (c) inoculating *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005) with 10% seed respectively into different fermentation tank; (d) culturing *Bifidobacterium longum* 6-1 (CCTCC Number M 98003) at a temperature of 37–38° C., a pressure of 0.3–0.6 kg/cm (inner) under anaerobic and nitrogenous conditions; culturing *Lactobacillus acidophilus* YIT 2004(CCTCC Number M 98004) and *Sterptococcus faecalis* YIT 0027(CCTCC Number M 98005) at the same temperature and pressure but with sterile gas; (e) separating the bacteria from the medium by centrifugation at 20000 rpm; (f) adding same amount of protective medium to the bacteria mud; (g) lyophilizing the composition; (h) mixing the lyophilized power with starch and pre-glued starch; and (I) preparing the lactic acid producing bacteria composition in forms of capsule, tablet or granule.

This invention provides the above methods for preparing a microbe composition wherein said protective medium comprises 10–20% dried skim milk, 10–20% lactulose, 0.01–0.2% sodium vitamin C, 0.01–2% sodium glutamate, 0.01–2% vitamin E, 6–20% β-cyclodextrin and 6–20% starch.

This invention provides the above methods for preparing a microbe composition wherein said protective medium comprises 10–20% dried skim milk, 10–20% lactulose, 0.01–0.2% sodium vitamin C, 0.01–2% sodium glutamate, 0.01–2% vitamin E and 6–20% starch.

This invention provides the above methods for preparing a microbe composition wherein said protective medium comprises 10–20% lactulose, 0.01–0.2% sodium vitamin C, 0.01–2% vitamin E and 6–20% starch.

This invention provides an zymotic fluid comprising skim milk, glucose, ammonia sulfate, monopotassium phosphate, dipotassium hydrogen phosphate and calcium carbonate.

This invention provides an zymotic fluid comprising skim milk, glucose, yeast powder, ammonia sulfate, monopotassium phosphate, dipotassium hydrogen phosphate and calcium carbonate.

This invention provides an oral formulation containing the above microbe compositions.

This invention provides the above oral formulation that can take the form of pill, capsule, tablet, granule or a suspension.

This invention provides a method for balancing intestinal flora in a subject comprising administering to the subject an effective amount of the above microbe compositions.

This invention provides a method for inhibiting the growth of *Shigella sonnei* and *Shigella flexneri* comprising contacting an effective amount of the above microbe compositions with *Shigella sonnei* and *Shigella flexneri*.

This invention provides a method for treating various kinds and degrees of diarrhea in a subject comprising administering to the subject an effective amount of the above microbe compositions.

This invention provides a method for treating constipation in a subject comprising administering to the subject an effective amount of the above microbe compositions.

This invention provides a method for regulating and enhancing immunologic function in a subject by increasing the serum complement 3 (C3) level comprising administering to the subject an effective amount of the above microbe compositions.

This invention provides a method for regulating and enhancing immunologic function in a subject by promoting specific antibody formation comprising administering to the subject an effective amount of the above microbe compositions.

This invention provides a method for regulating and enhancing immunologic function in a subject by activating proliferation of B and T lymphocytes comprising administering to the subject an effective amount of the above microbe compositions.

This invention provides a method for decreasing the level of plasma endotoxin in a subject comprising administering to the subject an effective amount of the above microbe compositions.

This invention provides a method for decreasing the level of abnormally elevated cytokine IL-6 in a subject comprising administering to the subject an effective amount of the above microbe compositions.

This invention provides a method for improving and enhancing liver function by decreasing serum alanine transaminase (ALT) level in a subject comprising administering to the subject an effective amount of the above microbe compositions.

This invention provides a method for improving and enhancing liver function by decreasing serum AUT level in a subject comprising administering to the subject an effective amount of the above microbe compositions.

This invention provides a method for improving and enhancing liver function by decreasing serum AST level in a subject comprising administering to the subject an effective amount of the above microbe compositions.

This invention provides a method for improving and enhancing liver function by decreasing serum bilirubin (SB) level in a subject comprising administering to the subject an effective amount of the above microbe compositions.

This invention provides a method for improving and enhancing liver function by decreasing serum globulin level in a subject comprising administering to the subject an effective amount of the above microbe compositions.

This invention provides a method for improving and enhancing liver function by increasing serum albumin level in a subject comprising administering to the subject an effective amount of the above microbe compositions.

This invention provides a method for treating acute hepatitis in active stage in a subject, especially when it is accompanied with endotoximia comprising administering to the subject an effective amount of the above microbe compositions.

This invention provides a method for treating chronic hepatitis in active stage in a subject, especially when it is accompanied with endotoximia comprising administering to the subject an effective amount of the above microbe compositions.

This invention provides a method for alleviating liver injuries including swelling, degeneration and necrosis in a subject comprising administering to the subject an effective amount of the above microbe compositions.

This invention provides a method for alleviating liver cirrhosis in a subject comprising administering to the subject an effective amount of the above microbe compositions.

The present invention is further explained by way of the following examples which are to be construed as merely illustrative and not limitative of the remainder of the disclosure in any way whatsoever.

EXAMPLE 1

Preparing the Microbe Composition in the Formulation of Capsule

Dissolving 7 kg. of skim milk powder, 12 kg. of glucose, 500 g. of yeast powder in three containers respectively with 200 kg. Of water, adjusting pH to 6.5. Sterilizing at the temperature of 1210C for 10 minutes, then inoculating 10% *Bifidobacterium longum* 6-1 (CCTCC Number M 98003) in each container, culturing at the temperature of 37° C. under anaerobic condition for 18 hours, then cooling down. *Lactobacillus acidophilus* YIT 2004 (CCTCC Number M 98004) and *Sterptococcus faecalis* YIT 0027 (CCTCC Number M 98005) are cultured at the temperature of 37° C. under aerobic condition for 20 hours and let to cool. 8 kg. of bacterium mud are collected by centrifugation. Then it is mixed with protective materials and lyophilized at the temperature of –40° C., that produce about 5 kg. of lyophilized powder. The three kinds of bacterium powder are mixed with 20 kg. Of compressible starch and 400 g. of magnesium myristin, which is then sifted through #40 mash and filled into capsules directly.

No. 1 formulation for lyophilized protective material includes 2 kg. of Skim milk powder, 400 g. of sodium glutamate and 3 kg. of lactulose dissolved in 12 kg. of water and sterilized at the temperature of 121° C. for 15 minutes.

EXAMPLE 2

Preparing the Microbe Composition in the Formulation of Tablet

Dissolving 10 kg. of skim milk powder, 2 kg. of glucose, 1 kg. of yeast powder, 500 g. of ammonia sulfate, 150 g. of $KH_2PO_4$, 300 g. of $K_2HPO_4$ with 200 kg. of water, adjusting pH to 7.0. Sterilizing at the temperature of 121° C. for 10 minutes. Then proceeding as example 1, after mixing the three kinds of lyophilized bacterium powder, combine the mixture with 2 kg. of cyclodextrin and the mixture is then grinded. Combine the mixture with 20 kg. of compressible starch and 2 kg. of lactose, that is sifted through #40 mesh and pressed into tablets.

No. 2 formulation for lyophilized protective material includes 2 kg. of skim milk powder, 20 g. of Vitamin E, 3 kg. of lactulose and 30 g. of sodium vitamin C dissolved in 12 kg. of water and sterilized at the temperature of 121° C. for 10 minutes.

EXAMPLE 3

Preparing the Microbe Composition in the Formulation of Granule

Dissolving 7 kg. of skim milk powder, 1.2 kg. of glucose and 500 g. of yeast powder with 200 kg. of water, adjusting pH to 7.0. Sterilizing at the temperature of 121° C. for 10 minutes. Then proceeding as example 1, after mixing the three kinds of lyophilized bacterium powder, combine the mixture with 17 kg. of granulose milk prepared with 0.1% of HPMC solution. The mixture is then sifted through #12 mesh and packaged with aluminum plastics.

No. 3 formulation for lyophilized protective material is the same as No. 1.

EXAMPLE 4

Preparing the Microbe Ccomposition in the Formulation of Tablet

Dissolving 8 kg. of skim milk Powder, 2 kg. of glucose and 1 kg. of yeast powder with 200 kg. of water, adjusting pH to 7.0. Sterilizing at the temperature of 121° C. for 10 minutes. Then proceeding as example 1, after mixing the three kinds of lyophilized bacterium powder, combine the mixture with 2 kg. of β-cyclodextrin, 16 kg. of compressible starch, 4 kg. of lactose and 4 kg. of ethyl-fibrin, which is next sifted through # 24 mesh and pressed into tablets.

No. 4 formulation for lyophilized protective material is the same as No. 2.

EXAMPLE 5

Preparing the Microbe Composition in the Formulation of Capsule

Dissolving 7 kg. of skim milk powder, 1.2 kg. of glucose and 500 g. of yeast powder with 200 kg. of water, adjusting pH to 6.5. Sterilizing at the temperature of 121° C. for 10 minutes. Then proceeding as example 1.

EXAMPLE 6

Preparing the Microbe Composition in the Formulation of Granule

Dissolving 10 kg. of skim milk powder, 2 kg. of glucose, 1 kg. of yeast powder, 500 g. of ammonium sulfate, 150 g.

of KH$_2$PO4 and 300 g. of K$_2$HPO$_4$ 200 kg. of water, adjusting pH to 7.0. Sterilizing at the temperature of 121° C. for 10 minutes, then proceeding as example 1, after mixing the three kinds of lyophilized bacterium powder, admix 2 kg. of β-cyclodextrin with the mixture and the mixture is then grinded. Admixing the mixture further with 17 kg. of granulose milk prepared with 0.1% HPMC solution. The mixture is then sifted through #12 mesh and packaged with aluminum plastics.

No. 6 formulation for lyophilized protective material is the same as No. 2.

EXAMPLE 7

Toxicity Experiment

The microbe composition of this invention has been proved to be safe to use by the following toxicity tests.

1. Whole body toxicity test: the microbe composition was dissolved and diluted with hot sterile saline; each test mouse is given 1.6 million viable microbes (more than 4,000 times the dosage per kg. human body) via intravenous injection of tail vein, intra-peritoneal injection and gavage administration (3 groups, 20 mice/group, weight 20–25 g. 50% male and 50% female); observe for 7 days.

2. Seven day continuous toxicity test: each test mouse was given 2.9 million viable *Bifidobacterium longum* 6-1 (CCTCC Number M 98003) (equal to 7,000 times the dosage per kg. human body) via gavage administration; also test mouse was given the microbe composition containing 36 million viable bacteria (equal to 90,000 time the dosage per kg. human body) by the same administrative route; saline was used as control (20 mice/group, weight 20–25 g. 50% male and 50% female); the medicine was administered everyday for 7 days.

3. Results of the toxicity test: test animals showed no adverse reaction and abnormal activities; food consumptions were normal; the animal's body weight increased; there was no significant difference in animalls weight change between the test group and the control; no animal died at the end of the whole body toxicity test and the seven day continuous toxicity test. The results show that *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005) in the microbe composition are nontoxic.

The calculation method for the toxicity tests was as follows: the average body weight for mice was calculated as 23 grams, the average weight for human being was set as 60 kilograms. The final dosage for human being was 106 CFU/person/day.

(a) V.C./kg. (mice)=V.C. contained in the dosage for each mouse×1000/23 =1.6×10$^6$×1000/23=6.96×10$^7$ V.C./kg.

(b) V.C./kg. (body weight for human being)=dosage during the treatment/60=10$^6$/60=16666 V.C./kg.

a/b=4176

V.C. stands for viable count.

EXAMPLE 8

Toxicity Experiment

Experimental Animals: 3 dogs with weight of 10 kg. (No.1), 12 kg. (No. 2) and 12 kg. (No. 3) respectively.

Experimental Materials: the microbe composition of this invention in the form of capsule. Each capsule contains 210 mg. of powder with 4×10$^6$ CFU of *Bifidobacterium longum* 6-1 (CCTCC Number M 98003), 4×10$^6$ CFU of *Lactobacillus acidophilus* YIT 2004 (CCTCC Number M 98004) and 2×10$^7$ CFU of *Sterptococcus faecalis* YIT 0027 (CCTCC Number M 98005).

Administration Route: oral administration and observation for 3 days.

Dosage: 210 mg×50 (50 times the dosage for human) to dog No. 1; 210 mg.×24 (20 times the dosage for human) to dog No. 2; 210 mg.×12 (10 times the dosage for human) to dog No. 3;

Experimental Results: no abnormality of the nerve system, the cardiovascular system, the respiratory frequency or death was observed after administering the microbe composition to the three dogs orally with large, middle or small dosage.

EXAMPLE 9

Antagonistic Effect of the Microbe Composition of This Invention on *Shigella sonnei* and *Shigella flexneri*

Purposes of the Experiment: to test the antagonistic effect and to find out the mechanism of *Bifidobacterium longum* 6-1 (CCTCC Number M 98003), *Lactobacillus acidophilus* YIT 2004 (CCTCC Number M 98004), *Sterptococcus faecalis* YIT 0027 (CCTCC Number M 98005) and the combination of these three strains of microbe on enteric pathogenic bacteria *Shigella sonnei* and *Shigella flexneri*.

Experimental Materials:(1) strains of bacteria: *Bifidobacterium longum* 6-1 (CCTCC Number M 98003), *Lactobacillus acidophilus* YIT 2004 (CCTCC Number M 98004), *Sterptococcus faecalis* YIT 0027 (CCTCC Number M 98005) and the combination of these three strains of microbe and *Shigella sonnei* 73 and *Shigella flexneri* 301; (2) media: PYG broth, BL Agar and LB Agar; (3) facilities: aerobic and anaerobic culture facility, test tube, flask pipette, plat etc.

Experimental Methods: all strains of bacteria tested are cultured under the same condition and PYG broth is used as culture medium after pretest; all strains tested grow well under anaerobic condition at the temperature of 37° C. and the growth curves of the strains under such condition are plotted.

1. The antagonistic effects of *Bifidobacterium longum* 6-1 (CCTCC Number M 98003) on *Shigella sonnei*.

(1) Preparation of *Shigella sonnei* solution: inoculate *Shigella sonnei* (about 10$^3$ CFU/ml.) to a flask containing 100 ml. of PYG broth and culture under anaerobic condition at the temperature of 37° C. for 5 hours (this is the middle log phase); distribute the broth to 12 test tubes (6 ml. each) and divide the test tubes into four groups numbered as A, B, C and 0 (3 test tubes for each group).

(2) Preparation of *Bifidobacterium longum* 6-1 (CCTCC Number M 98003) solution: inoculate *Bifidobacterium longum* 6-1 (CCTCC Number M 98003) (about 10$^3$ CFU/ ml.) to a flask containing 50 ml. of PYG broth and culture under anaerobic condition at the temperature of 37° C. for 16 hours (this is the middle log phase) to obtain broth No. 1; diluting broth No. 1 with PYG broth to obtain broth No. 2 (10$^{-1}$) and broth No. 3 (10$^{-2}$) respectively.

(3) Mix-culture: Mix equal volume of broth 1, 2, 3 with equal volume of broth A, B and C; add 6 ml. of PYG broth to group 0 (three test tubes) as control and plat it out on LB medium for colony counting. This counting represents the value of *Shigella sonnei* at the beginning (0 hour) of each testing group; plating broth 1 out on LB medium for colony counting and then the value of *Bifidobacterium longum* 6-1 (CCTCC Number M 98003) in group A, B and C at 0 hour is obtained.

Culture the four groups mentioned above (12 test tubes) under anaerobic condition at the temperature of 37° C. and sample to plat out on BL medium for counting at different time.

2. The antagonistic effects of *Lactobacillus acidophilus* YIT 2004 (CCTCC Number M 98004) and *Sterptococcus faecalis* YIT 0027 (CCTCC Number M 98005) on *Shigella sonnei*.

(2) Preparation of *Lactobacillus acidophilus* YIT 2004 (CCTCC Number M 98004) and *Sterptococcus faecalis* YIT 0027(CCTCC Number M 98005) solutions: inoculate *Lactobacillus acidophilus* YIT 2004(CCTCC Number M 98004) and *Sterptococcus faecalis* YIT 0027 (CCTCC Number M 98005) (about 1 03 CFU/ml.) to two flasks containing 50 ml. of PYG broth each and culture under anaerobic condition at the temperature of 37° C. for 11 and 5 hours respectively, that are the middle log phase for *Lactobacillus acidophilus* YIT 2004 (CCTCC Number M 98004) and *Sterptococcus faecalis* YIT 0027 (CCTCC Number M 98005) respectively; mix equal volume of these two portions of broth to obtain broth No. 1; diluting broth No. 1 by PYG broth to obtain broth No. 2 ($10^{-1}$) and broth No. 3 ($10^{-2}$) respectively.

(3) Mix-culture: same as described above.

3. The antagonistic effects of the microbe composition comprising three lactic acid producing bacteria consisting essentially of *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005) on *Shigella sonnei* and *Shigella flexneri*.

(2) Preparation of suspension of the microbe composition comprising three lactic acid producing bacteria consisting essentially of *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005): mix 5 g. of the composition under sterile condition with 45 ml. of PYG broth to homogeneous state to obtain suspension No. 1; dilute suspension No. 1 with PYG broth to 10 times the volume to obtain the system suspension.

(3) Mix-culture: same as described above.

Experimental Results: the microbe composition shows significant antagonism against *Shigella sonnei* and *Shigella flexneri* in test tube by killing all bacteria of these two strains within 48 hours. The MIC of the microbe composition is 0.5–1 mg/ml.

The three bacterial strains in the composition display significant time sequential and synergetic features of their inhibitory effects. *Lactobacillus acidophilus* YIT 2004 (CCTCC Number M 98004) and *Sterptococcus faecalis* YIT 0027 (CCTCC Number M 98005) exhibit their inhibitory effects first. Then *Bifidobacterium longum* 6-1 (CCTCCNumber M 98003) shows its effect.

EXAMPLE 10

The Effect of the Microbe Composition of This Invention on Enhancing Immunologic Function and Protecting Liver Function Purpose of the Experiment To study the immunoenhancing and hepatoprotective effect of the microbe composition of this invention by using animal models and by comparing its effect with that of two other similar medicines—Lizhu Changle from Lizhu pharmaceutical Company in China and New Shin Biofermin produced by Takeda Chemical Industries, Ltd. of Japan.

Experimental Materials

1. The microbe composition of this invention in the formulation of granule with $1\times10^8$ viable microbes per gram of granule and two grams of granule per sachet. The ratio among *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005) was 1:1:1. The batch number was 960802 and the expiration date was Aug. 31, 1997.

2. Lizhu Changle: *Bifidobacterium longum* composition in the formulation of capsule with $5\times10'$ viable microbes per capsule (0.7 g.). The batch number was 960719 and the expiration date was Jul. 31, 1997. Lizhu Changle is a medicine produced by Lizhu Health Products Factory, Lizhu Traditional Chinese Medicine Factory, located at North Guihua Road, Gongbei, Zhuhai Special Economic Zone, Guangdong Province, P.R.C. Its telephone number is 86-0756-88744190.

3. New Shin Biofermin: A microbe composition comprising three lactobacilli: *Bifidobacterium longum, Acidophil lactobacilli* and *Sterptococcus faecalis* in the formulation of granule with $1\times10^8$ viable microbes per gram of granule. The batch number was 5No11 and the expiration date was December 1999. New Shin Biofermin is a medicine produced by Takeda Chemical Industries, Ltd., located at 1-1 Doshomachi 4-Chome Chuo-ku Osaka 541, Japan. Its telephone number is 06-204-2111.

Experimental Designs for the Immunological Studies

1. ICR female mice with body weight of 18–22 g. were randomized into 4 groups: one group for the microbe composition of this invention, one group for Lizhu Changle, one group for New Shin Biofermin and the last one as the control. The control group was administered only saline.

2. Fresh sheep red blood cells (SRBC) were washed 3 times with saline and 5% SRBC suspension was used as antigen for intraperitoneal injection of 0.2 ml. to each mouse.

3. Drug administration: All 3 drugs were administrated orally for 7 days. The low dosage is set according to human daily dosage and the middle and high dosage were set additionally.

4. Determinations were made 5 days after SRBC challenge. After bleeding, spleens and thymus of each mouse were weighed aseptically.

5. Antibody formation was tested by the method of quantitative hemolytic spectrophotometry (QHS). Fresh guinea pig serum was used as complement. $2\times10^7$ mouse splenocyte/ml was mixed with same volume of 5% SRBC and the mixture was incubated at 37° C. for one hour. After centrifugation, the optic density of the supernatants was read at 520 nm.

6. Lymphocyte proliferation was determined by the method of $^3$H-thymidine ($^3$H-TdR) incorporation. Mouse splenocyte were counted and diluted to $2\times10^6$ cells/ml. by using RPMI1640 culture medium with 10% fetal calf serum. 100 $\mu$L were dispensed into each well of a 96-well flat bottomed microtiter plate. Con A as T-lymphocyte mitogen was added to the wells to make the final concentration at 5 $\mu$g/ml. LPS as B-lymphocyte mitogen was added to other wells to make the final concentration at 10 $\mu$g/ml. The plates were incubated at 37° C. in a humidified atmosphere of 5% $CO_2$ for 72 hours. The lymphocyte proliferation was expressed by the incorporated radioactivity of $^3$H-TdR (9.25 kBq/well) which was added 15 hours before harvesting. The cells were collected on filter paper with a multiple tips collector and counted with a scintillator. The stimulation index was calculated as: SI=dpm of experimental well/dpm of control well.

7. Serum complement 3 (C3) levels were determined by simple immuno-diffusion method by using anti-mouse C3 serum made by our laboratory.

Experimental Designs for Liver Protective Studies

Male Kunming mice with body weight of 22–26 g. were randomized into 3 groups: one group for the microbe composition of this invention, one group for Lizhu Changle and one group as the control. The control group was administered with only saline. $CCl_4$ was dissolved with oil to make a 0.25% solution and was administered intragastrically to mice at 10 ml/kg. The drugs and dosages were given as designed in the immunological studies. After 7 days, mice were bled. ALT (serum alanine transaminase) levels were determined by Reitman's method. Livers were examined pathologically. The degrees of liver injury were evaluated from mild to severe as 1 to 4 degree.

Results

Experimental results indicated that the microbe composition of this invention was very effective in promoting specific antibody formation. The composition also increased B and T lymphocyte proliferation. It had no marked effect on mouse thymus and spleen weight. Lizhu Changle also promoted the antibody formation but was not as effective as the microbe composition of this invention on other immune responses. The Japanese New Shin Biofermin had some immunoenhancing effects at lower doses, but it inhibited antibody production at high dosage.

TABLE 8

Comparison between the Microbe Composition of This Invention and Lizhu Changle of Their Imunoenhancing Effect

| Drug | Dosage g/kg | N | Body Weight (g) | mg/10 g (body weight) Spleen Index | mg/10 g (body weight) Thymus Index | QHS | Stimulation Index T | Stimulation Index B | C3 g/10 L |
|---|---|---|---|---|---|---|---|---|---|
| Control |  | 7 | 25 ± 1 | 59 ± 6 | 28 ± 10 | 28 ± 0 | 4.2 ± 2 | 12 ± 1 | 16 ± 3 |
| Composition | 3 | 6 | 25 ± 2 | 56 ± 9 | 30 ± 3 | 35 ± 1*** | 15.2 ± 3** | 10 ± 1*** | 18 ± 4 |
| Composition | 6 | 7 | 24 ± 2 | 73 ± 8* | 31 ± 6 | 29 ± 1 | 6.4 ± 2 | 12 ± 1 | 19 ± 2* |
| Composition | 9 | 5 | 25 ± 1 | 66 ± 16 | 27 ± 5 | 44 ± 1*** | 5.4 ± 1 | 14 ± 1 | 14 ± 3 |
| Changle | 0.7 | 6 | 25 ± 2 | 61 ± 8 | 31 ± 7 | 38 ± 2** | 7.4 ± 1 | 10 ± 2 | 13 ± 6 |
| Changle | 1.4 | 6 | 24 ± 2 | 61 ± 3 | 32 ± 7 | 41 ± 0*** | 4.9 ± 1 | 18 ± 2 | 16 ± 4 |
| Changle | 2.8 | 6 | 25 ± 2 | 60 ± 11 | 28 ± 7 | 36 ± 1*** | 3.8 ± 1 | 14 ± 2 | 13 ± 4 |

*P < 0.05, P < 0.01, *P < 0.001 compared with control

TABLE 9

Comparison between the Microbe Composition of This Invention and Japanese New Shin Biofermin of Their Immunoenhancing Effect

| Drug | Dosage g/kg | N | Body Weight (g) | mg/10 g (body weight) Spleen Index | mg/10 g (body weight) Thymus Index | QHS | Stimulation Index T | Stimulation Index B | C3 g/10 L |
|---|---|---|---|---|---|---|---|---|---|
| Control |  | 6 | 25 ± 1 | 69 ± 7 | 28 ± 5 | 24 ± 1 | 2.8 ± 1 | 2.3 ± 0 | 18 ± 1 |
| Composition | 3 | 6 | 24 ± 1 | 88 ± 31 | 22 ± 4 | 24 ± 2 | 2.8 ± 0 | 2.0 ± 0 | 18 ± 1 |
| Composition | 6 | 6 | 24 ± 1 | 65 ± 10 | 31 ± 5 | 56 ± 2*** | 18.6 ± 6* | 3.0 ± 0 | 18 ± 2 |
| Composition | 9 | 6 | 23 ± 1 | 62 ± 13 | 27 ± 14 | 22 ± 2 | 4.3 ± 0 | 2.0 ± 0 | 2.0 ± 1 |
| Shin Biofermin | 1.5 | 6 | 23 ± 1 | 63 ± 12 | 29 ± 8 | 40 ± 2*** | 22.1 ± 0*** | 3.7 ± 0* | 21 ± 2 |
| Shin Biofermin | 3 | 5 | 21 ± 3 | 90 ± 25 | 23 ± 8 | 52 ± 1*** | 7.1 ± 0*** | 2.7 ± 0 | 23 ± 3* |
| Shin Biofermin | 6 | 5 | 23 ± 3 | 66 ± 7 | 23 ± 9 | 20 ± 1** | 5.3 ± 1** | 2.2 ± 0 | 23 ± 3* |

*P < 0.05, P < 0.01, *P < 0.001 compared with control

In liver intoxicated animal models, the microbe composition of this invention decreased Serum alanine transaminase (ALT) level by a significant amount in all dosages tested. Pathological findings also showed that the microbe composition of this invention alleviated liver injuries such as cell swelling, degeneration and necrosis. In some cases, liver slices remained almost as normal. The control drug did not show such effects.

TABLE 10

Effect of the Microbe Composition of this Invention on Liver Function and Injuries

| Drug | Dosage | N | Route | ALT (Karmen Unit) | Liver Injury |
|---|---|---|---|---|---|
| Control | | 9 | po | 223 ± 22 | 2.4 ± 0.8 |
| Composition | 3 | 8 | po | 139 ± 59* | 1.5 ± 0.8* |
| Composition | 6 | 8 | po | 197 ± 16* | 2.0 ± 0.8 |
| Composition | 9 | 8 | po | 197 ± 18* | 1.8 ± 0.9 |
| Changle | 2.8 | 8 | po | 287 ± 21 | 1.9 ± 0.8 |

*$P < 0.05$

Conclusions

Animal experiments show that the microbe composition of this invention is effective in regulating and enhancing the immune function and the liver function of detoxification both functionally and morphologically.

The First Series of Clinical Study: The Effect of the Microbe Composition of This Invention on Treating Diarrhea and Constipation Selection Criteria for Patients Patients suffering various kinds and degrees of diarrhea and constipation were selected to participate in the clinical trials, that include:

1. Acute Diarrhea (1) Mild acute diarrhea: patients had a temperature below 38° C. and diarrhea for no more than 4–5 times/day; feces was in pulpy shape; no purulent discharge could be observed; culture of feces showed negative; there were no other significant clinical symptoms.

(2) Common acute diarrhea: patients had a temperature around 38–39° C. and diarrhea 5–15 times/day; there was purulent or mucus discharge; the number of leucocytes was below 20,000/ml.; patients remained fully conscious with normal cardiovascular and respiratory functions; there was no somnolent symptom.

(3) Acute diarrhea with no clear cause (including bacteria and virus); patients had detrimental eating and drinking habit; the disease occurred abruptly; patients had diarrhea for more than 3 times/day; there was no purulent discharge; the number of leucocytes was below 15 under micro bioscope.

2. Chronic diarrhea: patients had diarrhea for 2–3 times/day; the shape of feces had been abnormal for 2–3 months; the disease appeared repeatedly and appeared recently again.

3. Constipation: patients suffered from constipation and defecated only once for 2–3 days; the feces were dry and hard; patients often need laxative suppository or lubricant; the constipation had lasted for more than one week.

Design of the Clinical Trials

The clinical trials were designed by the Department of Digestive Internal Medicine and the Department of Clinical Pharmacology of Beijing Friendship Hospital in China according to "the Guideline for Digestive Drug Clinical Research" and "the Technical Requirements on Human Clinical Observation for New Biopreparation" issued by the Ministry of Health of the People's Republic of China. Double blind and open comparative methods were applied. Patients taking part in the clinical trials stopped using other drugs such as antibiotics, hormones, adsorbents, astringents or lubricants before the trials began. Standard forms were used to keep the record of the clinical trials data.

540 patients (including adults and children) participated in the clinical trials. Researchers randomized 401 patients into the test group and 139 patients into the control group. Patients in the test group were treated by the microbe composition of this invention in the formulation of capsule. Patients in the control group were treated by biofermin also formulated into capsule. There was no difference between the capsules in appearance. The dosage and administrative route were as follows: for adults, 5 capsules each time, 2–3 times a day; for children: $0^+$–1 years old, 1 capsule each time; 1–6 years old, 2 capsules each time; 6-13 years old, 3 capsules each time; all children took medicine 3 times/day. Capsules could be opened to mix powder with warm water for baby administration.

Data obtained from the clinical trials were processed according to Ridit and other statistical methods.

Results of the Clinical Trials

From the results of the clinical trials, it can be concluded:

1. The microbe composition of this invention is effective in treating various kinds of diarrhea. The total effective rate for the test group was 97.5% wherein the marked effective rate was 58.6% and the effective rate was 38.9%. The total effective rate for the control group was 50.4% wherein the marked effective rate was 22.3% and the effective rate was 28.1%.

TABLE 11

Effects of the Microbe Composition on Diarrhea ($P < 0.05$)

| Groups | Total Effective Rate | Marked Effective Rate | Effective Rate |
|---|---|---|---|
| Test | 97.5% | 58.6% | 38.9% |
| Control | 50.4% | 22.3% | 28.1% |

2. The microbe composition is more effective in treating acute diarrhea than chronic diarrhea.

TABLE 12

Comparison of the Effective Rates of the Microbe Composition on Acute Diarrhea and Chronic Diarrhea ($P < 0.05$)

| | Total Effective Rate | | Marked Effective Rate | |
|---|---|---|---|---|
| | Acute Diarrhea | Chronic Diarrhea | Acute Diarrhea | Chronic Diarrhea |
| Adults | 92.3% | 80.0% | 76.9% | 43.6% |
| Children | 90.7% | 76.3% | 59.0% | 39.0% |

3. In addition to treating diarrhea caused by unclear reasons, the microbe composition of this invention is also effective in treating infectious diarrhea caused by dysentery bacteria, salmonellae, pathogenic coliform bacteria, jejunum curved bacteria, pseudomonas aerogened and wheel-like virus. In the test group, 52 patients were determined as being infected by pathogens when they were selected to participate in the trials. 50 of them (96.2%) turned to negative after treatment by the microbe composition. The composition was also found markedly effective on all the 8 patients infected by wheel-like virus although they did not take virus detection test after the clinical trials. By contrast, in the control group, only 50% patients infected by pathogens turned to negative after treatment.

4. The microbe composition of this invention is effective in treating constipation. Of the six participating patients suffering constipation, the composition was found to be effective on 4 of them.

5. The microbe composition of this invention is effective in regulating intestinal flora. In the test group, 19 adults and 16 children were diagnosed to have intestinal flora disorder of different degrees before taking part in the clinical trials, mainly with the symptoms of both the number of enterobacteria such as aerobic or facultative anaerobic bacteria too high and the number of anaerobic bacteria such as Bifidobacteria too low. The intestinal flora of these patients recovered to normal condition after treatment by the microbe composition of this invention in the clinical trials.

6. The microbe composition of this invention has no side effects.

Expanded program of clinical trial phase III conducted at 80 hospitals in Beijing and Shanghai further tested the efficacy of the microbe composition in 1,321 patients, including 866 adults and 455 children. The total effective rate to treat acute diarrhoeal was 95.6% for adults and 91.3% for children. The total effective rate to treat chronic diarrhoea was 88.8% for grown-ups and 96.3% for children. The effective rate for treating bacillary dysentery is 94.2% for adults and 92.9% for children while 77.5–94.4% pathogen turn to negative.

The microbe composition was effective not only in treating diarrhoea, but also in restoring peristalsis in constipation cases. The composition can be given by rectum in addition to the common administrative route by mouth. At the clinical trials for treating constipation joined by 94 adults and 61 children, the composition was found to have a marked effective rate of 44.7% and 50.8% for each group while the total effective rate was 77.5% and 88.5% for each group respectively.

The Second Series of Clinical Study: The Effect of the Microbe Composition of This Invention on Treating Chronic Hepatitis B The microbe composition of this invention was used to treat 10 outpatients with chronic hepatitis B from August to November, 1996 at the Hepatic Section of Shuguang Hospital in Shanghai, the People's Republic of China.

Patient Selection 10 outpatients (8 male and 2 female) with the age from 26 to 60 took part in the clinical study. Their liver function test before treatment showed that AUT level was between 60–90 IU/l, serum bilirubin (SB) was abnormal in 3 cases, serum globulin was abnormal in 4 cases and HBV-DNA (PCR method) were all positive. All of the 10 patients had different degrees of abdominal distention, diarrhea, fatigue and dyschesia.

Treatment

The patients were treated by the microbe composition of this invention via oral administration. The dosage was 420 mg. each time and 3 times a day. The course of the treatment was 3 month.

Results

From the data obtained in the clinical study, it is concluded that the microbe composition of this invention is safe and effective in treating Chronic Hepatitis B.

1. The microbe composition of this invention is effective in improving liver function, especially in decreasing AUT level.

TABLE 13

Change of Liver Function before and after Treatment by the Microbe Composition of This Invention

|  | Before Treatment | | After Treatment | |
| --- | --- | --- | --- | --- |
|  | Normal | Abnormal | Normal | Abnormal |
| AUT | 0 | 10 | 9 | 1 |
| AST | 6 | 4 | 8 | 2 |
| SB | 6 | 4 | 6 | 4 |

2. The microbe composition of this invention is effective in decreasing serum globulin level.

TABLE 14

Change of Serum Globulin Level before and after Treatment by the Microbe Composition of This Invention

|  | Before Treatment | | After Treatment | |
| --- | --- | --- | --- | --- |
|  | Normal | Abnormal | Normal | Abnormal |
| A | 9 | 1 | 9 | 1 |
| G | 6 | 4 | 8 | 2 |
| A/G | 5 | 5 | 7 | 3 |

3. The microbe composition of this invention is effective in alleviating the clinical symptoms of chronic hepatitis B patients.

TABLE 15

Change of Chronic Hepatitis B Patients Clinical Symptoms before and after Treatment by the Microbe Composition of This Invention

|  | Abdominal Distention | Fatigue | Diarrhea | Dyschesia |
| --- | --- | --- | --- | --- |
| Before Treatment | 9 | 8 | 6 | 5 |
| After Treatment | 1 | 8 | 1 | 0 |

Discussion:

The microbe composition of this invention comprises the bacteria *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005). The three viable microbes are members of the normal flora in the intestine of healthy human being. Under normal circumstances, 85% of endotoxin can be detoxified by liver whereas hepatic cells and monocytes etc. are involved in the process of detoxification. The so-called monocyte clairvoyance system of patients with hepatitis is, to some extent, damaged and its detoxifying function greatly decreases, that would have a reverse effect on the detoxification of the toxic materials (including endotoxin) in intestine. In the meantime, the absorption of endotoxin will, in return, damage the liver. The effect is two-fold: on one hand, endotoxin will be non-specifically bound to hepatic cells. on the other hand, it will result in the dysfunction of hepatic cells and the blockage of energy metabolism by destroying the mitochondria and lysosome in hepatic cells, that would cause further deterioration of liver function and lead to a vicious cycle.

Of the three beneficial microbes of the composition, *Lactobacillus acidophilus* usually settles down in the upper part of colon, *Bifidobacterium longum* lives in the lower part of colon and *Sterptococcus faecalis* often dwells beyond the small intestine, forming an entire mycoderma barrier. Theoretically speaking, this barrier can sufficiently prevent the absorption of endotoxin and ammonia, thus improving liver function.

As for the 10 outpatients treated in the Shuguang Hospital in Shanghai, the AUT level of all the patients decreased to some extent and the AUT level of 9 patients returned to normal. The serum globulin of 4 patients also decreased while the symptoms of abdominal distension, diarrhea and dyschesia of 9 patients were apparently alleviated. The total bilirubin of 4 patients with icterohepatitis remained the same. The serum albumin of all of the 10 patients did not change and patients still suffered from fatigue. It is concluded that the microbe composition of this invention has supplementary effect in treating chronic hepatitis B.

The Third Series of Clinical Study: The Effect of the Microbe Composition of This Invention on Treating Chronic Viral Hepatitis The clinical study was performed by the Shanghai Hospital for Infectious Diseases from January to June, 1997.

Patients Selection 10 inpatients with chronic viral hepatitis (8 males and 2 females) at the Shanghai Hospital for Infectious Diseases were selected. The patients were from 24 to 69 years old and the mean value of their age was 43.5±16.1. According to the diagnostic standards revised at the Fifth National Conference on Infectious and Parasitic Diseases of China held in Beijing in May, 1995, these 10 patients were all diagnosed as with chronic viral hepatitis. Eight of them were diagnosed as with hepatitis B while the etiology for the other two was unknown. Of the ten patients, two were of mild severity, six were of moderate severity and the other two were of serious severity.

Designs of the Clinical Study

Medicine: The medicine used in this clinical study was the microbe composition of this invention in the formulation of granule packed in sachet. There were 2 g. of the microbe composition in each sachet containing $1 \times 10^7$ CFU *Bifidobacterium longum* 6-1 (CCTCC Number M 98003), $1 \times 10^7$ CFU *Lactobacillus acidophilus* YIT 2004 (CCTCC Number M 98004), $1 \times 10^7$ CFU *Sterptococcus faecalis* YIT 0027 (CCTCC Number M 98005), 200 mg. lactulose and 900 mg. skim milk powder.

In addition to the above mentioned microbe composition, vitamins and energy mixtures were used according to the needs of each patients. No other therapeutic drugs or traditional Chinese medicine were used in the course of treatment.

Method of Treatment: The microbe composition was administered orally with the dosage of 2 sachet each time and 3 times a day. The course of treatment lasted 8 weeks or ended earlier when patients were discharged from the hospital with recovered normal liver functions.

Observation Items: (1) changes of clinical symptoms of the patients, such as fatigue, diarrhea, nausea, vomit, abdominal distension and vague pain or discomfort in liver; (2) measurement of serum alanine transaminase (ALT), total bilirubin (SB), albumin and globulin every 2 weeks before and after the treatment; (3) measurement of protein electrophoresis, immunoglobulin, T cell subgroup and BCAA/AAA (branched-chain amino acid/aromatic amino acid).

Effect Evaluation: (1) Markedly Effective: indices of ALT and SB of the patients were reduced to normal level; (2) Effective: indices of ALT and SB of the patients were reduced by 50%; (3) No effect: indices of ALT and SB of the patients were reduced by less than 50%.

Results of the Clinical Study

Satisfactory results were achieved in the clinical study, that are shown in the following table:

TABLE 16

Results of the Clinical Study

| Total Cases | Marked Effective | Effective | No Effect |
|---|---|---|---|
| 10 | 7 | 1 | 2 |

1. Clinical Symptoms: Before treatment, eight patients out of the 10 had, in varying degrees, the symptoms of fatigue, diarrhea, nausea, vomit, abdominal distention, vague pain or discomfort in liver. Such symptoms disappeared in all eight patients after a period of 5–27 days of treatment, with the mean value of the course of treatment as 14±7 days.

2. Reduction of Serum ALT: Before treatment, ALT indices of the patients were 75–775 $\mu$/L with a mean value of 288.4±249 $\mu$/L. After a course of treatment of 2, 4, 6 and 8 weeks by the microbe composition of this invention, the mean value of ALT indices of the patients was reduced to 171±201 $\mu$/L, 121±153 $\mu$/L, 54.6±47.1 $\mu$/L and 52.7±59.5 $\mu$/L respectively. During the above mentioned periods, the ALT indices of 1, 4, 1 and 2 patients returned to normal respectively. The ALT indices of 2 patients were not markedly reduced at the end of the treatment (8 weeks).

TABLE 17

Effect of the Microbe Composition of This Invention on Reducing Serum ALT (Measured by Reducing the Mean Value of ALT Level on 10 Patients, $\mu$/L)

| Before Treatment | After 2 Weeks of Treatment | After 4 Weeks of Treatment | After 6 Weeks of Treatment | After 8 Weeks of Treatment |
|---|---|---|---|---|
| 288.4 ± 249 | 171 ± 201 | 121 ± 153 | 54.6 ± 47.1 | 52.7 ± 59.5 |

TABLE 18

Effect of the Microbe Composition of This Invention on Reducing Serum ALT (Measured by Reducing the Number of Patients with Abnormal ALT Level, out of 10 Hepatitis Patients Participating in the Clinical Study)

| Before Treatment | After 2 Weeks of Treatment | After 4 Weeks of Treatment | After 6 Weeks of Treatment | After 8 Weeks of Treatment |
|---|---|---|---|---|
| 10 | 9 | 5 | 4 | 2 |

3. Reduction of Serum SB: Out of 10 patients participating in the clinical study, the serum SB indices of 5 patients were abnormal before treatment, being 27.3–110.3 umol/L with the mean value of 41.04±40.45 umol/L. After a course of treatment of 2, 6 and 8 weeks by the microbe composition of this invention, the SB indices of 1, 1 and 2 patients returned to normal respectively. The SB level of 1 patient was reduced to 25.8 umol/L after 8 weeks of treatment.

TABLE 19

Effect of the Microbe Composition of This Invention on Reducing Serum SB (Measured by Reducing the Number of Patients with Abnormal SB Level, out of 10 Hepatitis Patients Participating in the Clinical Study)

| Before Treatment | After 2 Weeks of Treatment | After 4 Weeks of Treatment | After 6 Weeks of Treatment | After 8 Weeks of Treatment |
|---|---|---|---|---|
| 5 | 4 | 4 | 3 | 1 |

4. Other Laboratory Examinations: No significant difference was found between the examination results before and after the treatment of serum albumin, globulin, immunoglobulin, r-globulin, T cell subgroup, and BCAA/AAA.

5. No abnormal side effects were found during the course of treatment.

Discussion

Results of animal experiments have demonstrated that the microbe composition of this invention are effective in reducing ALT level in mice with liver function damage due to carbon tetrachloride and improving hepatic histology in mice and improving their immunological functions.

This clinical study further shows that the microbe composition of this invention has the property to reduce serum ALT and SB levels and to improve the clinical symptoms in hepatitis patients. The mechanism of these functions lies in the ability of the microbe composition of this invention to regulate the intestinal flora balance, to inhibit the growth of harmful bacteria and to reduce harmful agents production such as endotoxin, etc.

The Fourth Series of Clinical Study: The Effect of the Microbe Composition of This Invention on Intestinal Flora and Endotoxemia in Patients with Cirrhosis Purpose of the Clinical Study The purpose of this clinical study was to investigate the effect of the microbe composition of this invention on intestinal flora, endotoxemia and abnormally elevated cytokines in patients with cirrhosis.

Patients and Investigational Medicines 42 people took part in the clinical study and were divided into a test group and a control group.

The Test Group: 24 inpatients at the Renji hospital affiliated with the Second Medical University of Shanghai and the Center for Liver Diseases affiliated with the Nanjing Military Group of the People's Liberation Army participated in the clinical study. 20 patients were male and 4 were female. The patients were from 26 to 67 years old with the mean value of their age as 46. All patients had been diagnosed as with cirrhosis by abdominal ultrasonic examination and CT scanning and all of them showed typical clinical symptoms such as liver function abnormality and/or portal hypertension. 2 patients showed evident pathological changes. According to the Child-pugh categories, 13 patients had been classified as class Child B and 11 patients as class Child C. Patients with hemorrhage of digestive tract, repeated infections, concurrent liver cancer, severe hepatic encephalopathy and other organic failure in the last four weeks before the clinical study began were excluded.

Patients in the test group was further randomized into three subgroups:

(1) 9 patients in subgroup 1 were treated by the microbe composition of this invention in the formulation of capsules containing the protective medium lactulose.

(2) 8 patients in subgroup 2 were treated by the microbe composition of this invention in the formulation of capsules containing no lactulose.

(3) 7 patients in subgroup 3 were tested by a composition in the formulation of capsule containing only lactulose. Patients in three subgroups were not significantly different in age, sex and liver functions (bilirubin, albumin, ALT, AST). See Table 20 and 21.

TABLE 20

Distribution of Age (Mean Value) and Sex in 3 Test Subgroup ($P > 0.05$)

| Subgroup | Number | Age | Sex Male | Sex Female |
|---|---|---|---|---|
| Subgroup 1 | 9 | 47.01 ± 10.02 | 7 | 2 |
| Subgroup 2 | 8 | 45.88 ± 11.74 | 7 | 1 |
| Subgroup 3 | 7 | 49.57 ± 10.69 | 6 | 1 |

TABLE 21

Comparison of Liver Functions in 3 Test Subgroup ($P > 0.05$)

| Subgroup | Number | Albumin (g/L) | Bilirubin (umol/ml) | AST ($\mu$/L) | ALT ($\mu$/L) |
|---|---|---|---|---|---|
| Subgroup 1 | 9 | 27.60 ± 4.33 | 43.94 ± 52.13 | 78.33 ± 52.55 | 49.31 ± 43.31 |
| Subgroup 2 | 8 | 29.52 ± 5.19 | 50.10 ± 55.22 | 56.63 ± 24.66 | 50.13 ± 40.46 |
| Subgroup 3 | 7 | 26.30 ± 4.48 | 57.22 ± 68.56 | 76.29 ± 45.60 | 31.57 ± 8.06 |

The Control group: 18 healthy adults (11 male and 7 female) were selected as the control group. They were from 24 to 62 years old with the mean value of their age as 36. They all had no gastrointestinal, liver and gall disease by history inquiries and physical examination.

Design of the Clinical Study

Patients in the test group took the medicine as protocol specified orally three times a day and three capsules each time. The course of treatment lasted for three weeks. In addition to the medicines mentioned above, only a few basic medicines (such as vitamins, diuretics etc.) indispensable for treating cirrhosis were used. No patients received any antibiotics in the clinical study.

Quantitative tests were made on 7 common anaerobic and aerobic bacteria in the stool of 24 patients with cirrhosis before and after treatment. Measurement of endotoxin and cytokine IL-6 in peripheral blood was also conducted by ago-martial development process testing kit and ELISA respectively.

(1) Culture and Examination of Flora in Feces

Collection and dilution of samples: Proper fresh feces were put into a sterilized penicillin bottle by bacteria-free cotton stick. The bottle was placed into an anaerobic bag, then anaerobic generator. Afterwards, the sample was sent to the laboratory for separation and inoculation. 0.5 g. feces were taken into a sterilized bottle filled with glass beads, vibrated for mixture. The feces were then diluted into $10^{-11}$ by 10 times diluting methods and inoculated on selective media by using drip methods.

Culture: seven intestinal aerobic and anaerobic bacteria were screened for the study. Of these seven bacteria, 2 were aerobic bacteria (*E. coli*, Enterococci) while 5 were anaerobic bacteria (*Bifidobacterium longum*, Lactobacteria, Bacteroides, Eubacteria and *Bacillus perfringens*). Aerobic bacteria were inoculated at 37° C. for 24 hours whereas anaerobic bacteria were inoculated with Gasped ($CO_2/M_2$ generator) at 37° C. for 48 hours. The number of viable bacteria was calculated and expressed as the number of colony forming units per gram of feces.

Bacteria identification: Bacteria categories were initially identified by characteristics of the colony, Gram's stain, morphology under microscope and the specific medium. As for questionable bacteria, they were first separated from the colony, then cultured for further biochemical identification by micro biochemical plate reactions. Afterwards, the category of the bacteria was determined based on the determination list.

(2) Plasma Endotoxin Assay

The plasma endotoxin assay was conducted by agomatrical development process. The kit was provided by Shanghai Institute for Medical Laboratory Test. 0.1 ml. plasma treated by deinhibitory factor was mixed with 0.05 ml. reagent and incubated at 37° C. for 25 minutes. Then, 0.05 ml. tripeptide was added and incubated one more time for 3 minutes. After that, 0.5 ml. sodium nitrite, 0.5 ml. ammonium sulfamate and 0.5 ml. naphthyl ethylenediamine dihydrochloride were added. Absorption of the final mixture was measured at 545 nm. The content of endotoxin was calculated based on standard curves.

(3) IL-6 Assay

The assay was conducted according to the ELISA method. The IL-6 kit was a product manufactured by Belgian Medgenix (Tianjin) Sifang Biological Co.

Student't test was used for statistic analysis.

Results

1. Clinical symptoms such as abdominal distension, diarrhea and constipation, etc: the microbe composition of this invention used in subgroup 1 and 2 were very effective in alleviating the above-mentioned symptoms wherein the total effective rate was 89% and 85% respectively. The total effective rate in subgroup 3 was only 40%.

2. Intestinal Flora: the microbe composition of this invention is very effective in promoting the growth of intestinal anaerobic bacteria as well as inhibiting the proliferation of certain pathogens and/or potential pathogens, such as *E. coli*. The results were shown in the following table.

This table indicates that: (1) the number of *Bifidobacterium longum* and Bacteroides in patients with cirrhosis were much lower than in healthy people in the control while the number of *Bacillus perfringens* and *E. coil* in cirrhosis patients were higher than in people in the control ($P<0.05$); (2) for patients in the test subgroup 1, after three weeks of treatment by the microbe composition of this invention with lactulose, the number of *Bifidobacterium longum* and Bacteroides increased markedly ($P<0.05$) and the number of *Bacillus perfringens* decreased significantly ($P<0.05$); the number of *E. coli* was also reduced to some extent; (3) for patients in the test subgroup 2, after three weeks of treatment by the microbe composition of this invention with no lactulose, the number of *Bifidobacterium longum*, Bacteroides and Enterococci increased significantly ($P<0.05$) and the number of *E. coli* was decreased to some extent; (4) for patients in the test subgroup 3, the numbers of intestinal bacteria showed no significant change after three weeks of treatment by lactulose.

3. Plasma endotoxin and cytokine IL-6 levels: the microbe composition of this invention, by working together with lactulose, has the property of reducing the endotoxin and abnormally elevated cytokine IL-6 levels in cirrhosis patients.

TABLE 23

Changes of Plasma Endotoxin after Three Weeks of Treatment

|  | Control Group | Test Subgroup 1 | Test Subgroup 2 | Test Subgroup 3 |
|---|---|---|---|---|
| Before Treatment | 5.95 ± 0.61 | 10.32 ± 4.54* | 10.73 ± 2.09* | 9.7 ± 5.94* |
| After Treatment |  | 7.79 ± 3.51^ | 10.00 ± 2.38 | 8.79 ± 4.01 |

*Comparison with the control group, $P < 0.05$
^Comparison before and after treatment, $P < 0.05$

TABLE 22

Change of Intestinal Flora before and after Treatment

| Bacteria | Control Group N = 18 | Test Subgroup #1 N = 9 Before | Test Subgroup #1 N = 9 After | Test Subgroup #2 N = 8 Before | Test Subgroup #2 N = 8 After | Test Subgroup #3 N = 7 Before | Test Subgroup #3 N = 7 After |
|---|---|---|---|---|---|---|---|
| *Bifidobacterium longum* | 10.94 ± 1.32 | 7.64 ± 4.52* | 10.40 ± 1.98^ | 7.63 ± 5.06* | 9.85 ± 4.20^ | 9.19 ± 4.51 | 6.55 ± 4.61 |
| Lactobacteria | 8.95 ± 1.19 | 9.51 ± 1.29 | 9.32 ± 0.90 | 8.66 ± 1.17 | 9.63 ± 0.70 | 9.41 ± 0.94 | 9.07 ± 1.51 |
| Eubacteria | 9.30 ± 1.39 | 7.79 ± 4.51 | 9.45 ± 1.53 | 7.32 ± 4.59 | 9.67 ± 1.65 | 8.06 ± 3.96 | 9.28 ± 1.39 |
| Bacteroides | 9.27 ± 1.25 | 4.08 ± 4.85* | 8.01 ± 1.95^ | 4.77 ± 5.25 | 9.29 ± 1.93^ | 8.67 ± 4.15 | 7.21 ± 4.96 |
| *Bacillus perfringens* | 8.01 ± 0.73 | 9.74 ± 1.15* | 8.12 ± 1.32^ | 8.28 ± 1.54 | 8.66 ± 1.31 | 8.27 ± 1.18 | 9.28 ± 1.21 |
| Enterococci | 6.06 ± 1.02 | 7.13 ± 2.06 | 7.53 ± 2.06^ | 6.98 ± 1.47 | 8.31 ± 1.20^ | 6.42 ± 1.71 | 7.34 ± 1.84 |
| *E. Coli* | 7.21 ± 0.71 | 8.03 ± 1.83 | 7.22 ± 1.37 | 8.75 ± 1.99* | 7.77 ± 1.83 | 7.57 ± 2.15 | 7.45 ± 1.25 |

*Comparison with the control group $P < 0.05$
^Comparison with the bacteria quantities before and after treatment $P < 0.05$

TABLE 24

Changes of Cytokine IL-6 Level (pg./ml) after Three Weeks of Treatment

| | Control Group | Test Subgroup 1 | Test Subgroup 2 | Test Subgroup 3 |
|---|---|---|---|---|
| Before Treatment | 13.95 ± 0.61 | 26.58 ± 16.57* | 26.66 ± 17.35* | 28.37 ± 12.25* |
| After Treatment | | 20.92 ± 15.98^ | 23.09 ± 11.65 | 32.83 ± 23.04 |

*Comparison with the control group, P < 0.05
^Comparison before and after treatment, P < 0.05

The tables indicate that: (1) plasma endotoxin and cytokine IL-6 levels in patients with cirrhosis were much higher than people in the control (P<0.05); (2) after three weeks of treatment by the microbe composition of this invention with lactulose, plasma endotoxin and abnormally elevated cytokine IL-6 levels in patients in the test subgroup 1 were substantially decreased (P>0.05); (3) after three weeks of treatment by the microbe composition of this invention with no lactulose, plasma endotoxin and abnormally elevated cytokine IL-6 levels in patients in the test subgroup 2 were decreased to some extent (P>0.05); (4) after three weeks of treatment by lactulose, plasma endotoxin level in patients in the test subgroup 3 were decreased to some extent (P>0.05), but the abnormally elevated cytokine IL-6 level did not decrease.

4. Liver functions: the microbe composition of this invention can improve liver functions by significantly increasing the plasma albumin level.

TABLE 25

Changes of albumin after Three Weeks of Treatment

| | Test Subgroup 1 | Test Subgroup 2 | Test Subgroup 3 |
|---|---|---|---|
| Before Treatment | 27.60 ± 4.33 | 29.52 ± 5.19 | 26.30 ± 4.48 |
| After Treatment | 32.68 ± 5.97 | 37.93 ± 6.41 | 30.51 ± 4.29 |

P > 0.05

Discussion

Alteration of intestinal microflora, accompanied by impairment of intestinal mucosa's barrier function, makes the gut a reservoir of pathogens and/or potential pathogens, that plays an important role in the functional failure of multiple organs. It has been reported that many patients with chronic hepatic diseases, especially those with cirrhosis show, in varying degrees, imbalance of intestinal flora, with the number of *Bifidobacterium bifidum*, Bacteroides and Eubacteria being markedly reduced and the number of pathogens and/or potential pathogens such as *Bacillus perfringens* and *E. coli* significantly increased. These patients also often show clinical symptoms of abdominal distention, diarrhea and constipation, and are apt to enterogenous endotoxemia and spontaneous peritonitis. It has been indicated that the imbalance of intestinal flora has a positive correlation with the extent of liver functional damage.

Experiments in animals have shown that administration of exogenous *Bifidobacterium longum* and Lactobacteria could promote the growth of anaerobic bacteria, inhibit the proliferation of aerobic bacteria and confine bacterial translocation.—The microbe composition of this invention comprises *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005), that are beneficial to human beings. After oral administration of the microbe composition of this invention, the number of *Bifidobacterium longum* and Bacteroides in patients increased significantly and the number of *Bacillus perfringens* and *E. Coli* decreased to some extent, indicating that the microbe composition could not only compensate for the lack of *Bifidobacterium longum* in intestines but also support and promote the growth of other anaerobic bacteria such as Bacteroides. It has been shown by in vitro studies that *Bifidobacterium longum* can inhibit the growth of *E. Coli* and *Bacillus perfringens* when it is incubated together with the pathogens and/or potential pathogens, that is performed through various mechanisms such as production of acid metabolites and secretion of inhibiting factors. This clinical study verified the inhibiting effect of *Bifidobacterium longum* on pathogens and/or potential pathogens by preventing them from settling down on intestinal mucosa. Since the number of Lactobacteria does not decrease in patients with cirrhosis, it does not need to be supplemented by erogenous Lactobacteria. On the other hand, Lactobacteria can promote the growth of other anaerobic bacteria such as *Bifidobacterium longum* by lowering the environmental pH through its acid metabolites. In addition, it can secrete a protein-like adhesion stimulating factor, that would adhere to the cells of human intestinal mucosa and play a "barrier effect" function. This barrier effect can block the adhesion to or invasion of intestinal mucosa cells by intestinal pathogens and/or potential pathogens such as *E. Coli* and prevent them from overgrowth. As a result, the effect of the microbe composition of this invention is greatly reinforced by the coordinated function of *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005) in terms of time, space (different settling sites by bacteria) and metabolites.

This clinical study confirmed that the microbe composition of this invention could remarkably increase the number of intestinal *Bifidobacterium longum* and Bacteroides, and reduce the number of *E. Coli* and *Bacillus perfringens* in patients with cirrhosis. Administration of a small quantity of lactulose alone can not improve patient's intestinal flora.

The plasma endotoxin level in patients with cirrhosis is usually much higher than in people in the control. This is caused by damaged liver functions and direct entrance into systemic circulation by intestinal endotoxin that is not inactivated by stellate cells of liver due to protal- systemic shunt. The increase of intestinal endotoxin due to imbalance of intestinal flora or overgrowth of pathogens is one of the major causes responsible for endotoxemia in systemic circulation. It has been found that there is a positive correlation between the plasma endotoxin level and the number of *E.Coli* in patients. After a course of treatment by the microbe composition of this invention, plasma endotoxin levels in patients decreased, with the group treated by the microbe composition containing lactulose showing most marked effect. The mechanism for the reduction can be interpreted as follows: (1) addition of erogenous viable bacteria can compensate for the shortage or reduction of intestinal anaerobic bacteria such as *Bifidobacterium longum* and Bacteroides, improve the biological barrier effect of the intestinal mucosa, inhibit the growth of *E.Coli* and reduce endotoxin production; (2) the acid metabolites of viable bacteria such as lactic acid and acetic acid can reduce the pH value in intestinal cavity and inhibit the growth of *E.Coli*. When patient's plasma endotoxin level decreased, their liver function test took a favorable turn and the albumin level increased significantly. This is associated with the reduction of the effect of the endotoximia on liver when endotoxin level of the patient is decreased.

Cytokines such as TNF, IL-1 and IL-6 in blood circulation of patients with cirrhosis increased significantly. It has been found that the serum cytokine IL-6 level of patients participating in this clinical study was much higher than that of the people in the control. Since all of these patients were not suffering from other acute infection, the increase of serum cytokine IL-6 may be associated with plasma endotoxin concentration. Both in vitro studies and studies in animals have shown that endotoxin could induce the secretion of cytokine such as TNF and IL-6. The continued existence of endotoxemia in patients with cirrhosis may stimulate sustained excessive secretion of a cellular factor, which may, in return, exert effects through the induction of other cytokines, thus exacerbating the liver damage. It has been found that intestinal bacteria play an important role in regulating the response to diseases by cellular factors. The over-growth of some intestinal pathogens and/or potential pathogens such as E. coli may result in the sharp increase of plasma cytokine IL-6 after hemorrhagic shock. Therefore, the increase of cytokine IL-6 in patients with cirrhosis is closely related with the overgrowth of intestinal pathogens and/or potential pathogens such as *E. coli* and the increase of plasma endotoxin. Administration of the microbe composition of this invention to patients with cirrhosis can increase the number of intestinal anaerobic bacteria and decrease the number of *E. coli*, thus reducing plasma endotoxin and abnormally elevated cytokine IL-6 levels.

The reason why the microbe composition of this invention containing isolatose achieved the best results in reducing plasma endotoxin and abnormally elevated cytokine IL-6 levels might be as follows: although the use of small quantity of lactulose alone has no effect on patient's intestinal flora, plasma endotoxin and abnormally elevated cytokine IL-6 levels, a coordinated function is exerted when lactulose is used together with the beneficial bacteria of this invention. In certain circumstances, the beneficial bacteria could not propagate and exert effects in intestinal tract due to unfavorable environment such as high pH value. Lactulose, on the other hand, as a somatotrophic agent for the beneficial bacteria and an agent which can not be absorbed by intestines, can help the bacteria to settle down on intestines.

Conclusions

The microbe composition of this invention is effective in reducing the endotoxin levels in the blood of human being and further reducing cytokines reaction induced by endotoxin. The microbe composition of this invention has the property of improving liver functions by regulating the intestinal flora in patients with cirrhosis.

The Fifth Series of Clinical Study: The Effect of the Microbe Composition of This Invention on Intestinal Flora and Endotoxemia in Patients with Cirrhosis Purpose of the Clinical Study Since there is no specific therapy for endotoxemia at present, the purpose of this clinical study was to investigate the effect of the microbe composition of this invention on changes of intestinal flora and the relationship between intestinal flora and plasma endotoxin levels in patients with cirrhosis.

Design of the Clinical Study

Selection of Patients: 42 cirrhotic patients participated in the clinical study and were randomized into a treatment group and a control group. Distribution of patients in two groups is shown in the following table:

TABLE 26

Distribution of Patients

| Group | Number | Male | Female | Range of Age | Mean Age |
|---|---|---|---|---|---|
| Treatment | 24 | 21 | 3 | 27–64 | 46.8 |
| Control | 18 | 16 | 2 | 31–69 | 48.5 |

The following table shows the clinical data of the patients in two groups before treatment. There was no significant difference in age, sex and liver function between patients of the two groups.

TABLE 27

Clinical Data of the Patients before Treatment

| Group | Age mean | Sex Male/ Female | Albumin g/L | Bilirubin umol/ml | ALT U/L | AST U/L |
|---|---|---|---|---|---|---|
| Treatment | 46.8 | 21/3 | 31.74 ± 6.1 | 41.8 ± 44.33 | 46.79 ± 9.3 | 70.19 ± 42.18 |
| Control | 48.5 | 16/2 | 29.3 ± 6.52 | 49.24 ± 40.99 | 35.13 ± 19.3 | 38.4 ± 19.43 |

$P > 0.05$

Method of Treatment: Patients in the treatment group were orally administered the microbe composition of this invention in the formulation of capsule, three capsules each time and three times a day in addition to basic therapy. The control group received only basic therapy. No patients received any antibiotics or other agents which may effect intestinal flora during the study. The course of treatment was three weeks.

Method of Analysis: Feces from the patients were cultured aerobically and anaerobically. Feces bacteria were quantitatively analyzed with Gas-Pak while plasma endotoxin concentrations were determined with a Limulus assay. Bacteriological Analysis of Feces: Seven representative bacteria in feces of the patients were analyzed quantitatively, that included two aerobic bacteria (*Escherichia coli* and Enterococci) and five anaerobic bacteria (Bifidobacteria, Lactobacteria, Eubacteria, Bacteroides and *Clostridium Perfringens*). Serial 1:10 dilution of the feces was plated onto selective media. All the media for aerobic bacteria were incubated at 37° C. for 24 hours whereas anaerobic bacteria were incubated with Gas-pak (CO2/H2 generator) at 37° C. for 48 hours. Anaerobic bacteria were identified by AN-IDENT system (BioMerieux, France). The number of living bacteria was calculated and expressed as the number of colony forming units per gram of feces.

Plasma Endotoxin Assay: The heated plasma (0.1 ml) was added to 0.05 Limulus lysate and incubated at 37° C. for 25 minutes. At the end of this period, 0.05 ml of Boc-Leu—Gly-Arg-PNA was added and incubated for an additional 3 minutes at 37° C. Then 0.5 ml sodium nitrite, 0.5 ml amino benzene sulfonic acid ammonium salt and 0.5 ml naphthyl ethylenediamine dihydrochloride were added to mixture. Absorption of the final mixture was measured at 545 nm.

Statistics: All values were expressed as means±SEM. Student t was used.

Results of the Clinical Study

After oral administration of the microbe composition of this invention, clinical manifestations of the patients, such as abdominal pain, diarrhea and constipation were significantly reduced or disappeared in about 88% patients in the treatment group as compared with only 39% patients in the control group.

The intestinal flora also had significant changes after three week treatment with the microbe composition of this invention. The number of Bifidobacteria, Bacteroides and Eubacterium increased significantly and the number of *Escherichia coli* and *Clostridium perfringens* decreased in the treatment group. In addition, the plasma endotoxin level of the patients also decreased markedly after treatment. There was no significant improvement in the control group. A significant correlation was observed between plasma endotoxin levels and the number of *E.Coli* in cirrhotic patients.

TABLE 28

Changes of Intestinal Flora before and after Treatment by the Microbe Composition of This Invention

| Bacterial | Treatment Group | | Control Group | |
|---|---|---|---|---|
| | Before ($lg^n/g$) | After ($lg^n/g$) | Before ($lg^n/g$) | After ($lg^n/g$) |
| Bifidobacteria | 7.64 ± 4.28 | 10.03 ± 2.86* | 7.61 ± 4.68 | 7.44 ± 3.73 |
| Lactobacteria | 9.14 ± 1.16 | 9.35 ± 1.17 | 9.20 ± 1.58 | 9.30 ± 1.39 |
| Eubacteria | 7.49 ± 4.16 | 9.34 ± 1.40* | 5.88 ± 4.44 | 7.47 ± 2.89 |
| Bacteroides | 5.31 ± 4.68 | 8.50 ± 2.56* | 5.76 ± 4.94 | 5.11 ± 4.89 |
| C. perfringens | 8.76 ± 1.39 | 7.69 ± 1.60* | 8.02 ± 1.30 | 8.62 ± 1.39* |
| Enterococci | 6.92 ± 1.62 | 7.17 ± 1.84 | 6.64 ± 1.59 | 7.49 ± 1.50* |
| E. Coli | 8.08 ± 1.48 | 7.33 ± 1.38* | 8.07 ± 1.65 | 8.46 ± 1.46 |

*$p < 0.05$

The plasma endotoxin levels were similar in patients of the two groups before treatment (9.49±3.51 pg/ml vs 9.62±4.83 pg/ml). After three weeks of treatment, the plasma endotoxin levels in the treatment group decreased significantly (7.88±3.23 pg/ml vs 9.49±3.51 pg/ml, p<0.05). By contrast, there was no change of the plasma endotoxin levels in the control group (10.02±5.41 pg/ml vs 9.62±4.83 pg/ml, p>0.05).

Discussion

Alteration of intestinal microflora, combined with impairment of intestinal mucosal barrier function, makes the gut the reservoir of potential pathogenic bacteria. Some other previous studies have found that the balance of intestinal flora was disturbed in patients with cirrhosis. The number of Bifidobacteria, Eubacteria and Bacteroides decreased significantly with an overgrowth of *Escherichia coli* and *Clostridium perfringens*. The degree of intestinal flora disturbance is correlated with the severity of liver dysfunction and occurrence of ascites.

Some other previous studies in animal have shown that administration of exogenous Bifidobacteria and Lactobacteria can promote the growth of anaerobic bacteria and inhibit proliferation of aerobic bacteria and confine bacterial translocation. This clinical study find that after oral administration of the microbe composition of this invention for three weeks, the number of Bifidobacteria, Bacteroides and Eubacteria in feces increased significantly and the number of *Escherichia coli* and *Clostridium perfringens* decreased in the treatment group. There was no significant improvement in patients in control group. The *Clostridium perfringens* even increased. These data indicated that the microbe composition of this invention can not only supply for Bifidobacteria but also promote the growth of other anaerobic bacteria which have been diminished. The mechanisms for this effect may include production of acid metabolites and bacteriocins, secretion of some inhibiting factor to prevent potential pathogenic bacteria attachment to the mucus and overgrowth, lowering PH of intraluminal. Since the indigenous anaerobic bacteria are not sufficient to maintain the balance of the enteric bacterial ecology, it is important to give exogenous beneficial bacteria to reconstitute the gut flora to its normal composition and increase colonization resistance.

The plasma endotoxin levels in patients with cirrhosis were higher than people in healthy conditions. It has been found that there is a positive correlation between plasma endotoxin levels and the number of *Escherichia coli*. This clinical study shows that the plasma endotoxin levels decreased in the treatment group after three weeks of administration of the microbe composition of this invention. Mechanism of the composition for this reduction may be found in its following functions: (1) modulating the intestinal flora by promoting anaerobic bacteria and inhibiting *E. coli* and subsequently reducing the production of endotoxin; (2) increasing intestinal motility to prevent enteric bacteria overgrowth; (3) producing acid metabolites to low intralimunal PH to inhibit *E. coli* growth.

Conclusions of the Clinical Study

The normal intestinal microflora of human being is relatively stable, but may be disturbed in pathologic conditions. In cirrhotic patients, anaerobic bacteria decrease and aerobic bacteria increase. The overgrowth of aerobic gram-negative bacteria plays an important role in the development of endotoxemia in cirrhosis. The microbe composition of this invention has beneficial effect on intestinal flora of patients with cirrhosis by promoting the growth of anaerobic bacteria and inhibiting proliferation of gram-negative aerobic bacteria. Therefore the microbe composition can reduce production of endotoxin in patients with cirrhosis.

Reference

1. Friend B. Shahani, K.: Nutritional and Therapeutic Aspects of Lactobacilli. Journal of applied Nutrition 36, 125–153; Hamdan I.: Acidolin and Antibiotic Produced by Acidophilus. Journal of Antibiotics 8, 631–636.
2. Vandenbergh P A: Lactic Acid Bacteria, Their Metabolic Products and Interference with Microbial Growth. FEMS Microbiol. Review 12, 221–38 1993; Fernandes C. et al: Control of Diarrhoea by Lactobacilli. Journal of Applied Nutrition 40, 32–42, 1988.
3. Shehani K.: Role of Dietary Lactobacilli in Gastrointestinal Microecology. American Journal of Clinical Nutrition 33, 2248–2257.
4. de Simone C.: Microflora, Yogurt and the Immune System. Int. J. Immunotherapy II, 19–23 1986; Marteau P. & Rambaud J C: Potential of Using Lactic Acid Bacteria for Therapy and Immunomodulation in Man. FEMS Microbiol. Reviews 12, 207–20, 1993.
5. Reddy G.: Antitumour Activity of Yogurt Components. Journal of Food Protection 46, 8–11 1983; Fernandes C F & Shahani K M: Anticarcinogenic and immunological Properties of Dietary Lactobacilli. Journal of Food Protection 53, 704–710, 1990.
6. Kampman E, Goldbohm R A, van den Brandt P A & van't Veer P: Fermented Dairy Products, Calcium, and Colorectal Cancer in the Netherlands Cohort Study. Cancer Res. 54, 3186–3190, 1994.
7. Goldin B R & Gorbach S L: The Effect of Milk and Lactobacillu Feeding on Human Intestinal Bacterial Enzyme Activity. Am. J. Clin. Nutr. 39, 756–61, 1984; Marteau P, Pochart P, Flourie B, Pellier P, Santos L. Desjeux J F & Rambaud J C: Effect of Chronic Ingestion of a Fermented Dairy Product Containing *Lactobacillus acidophilus* and *Bifidobacterium bifidum* on Metabolic Activities on the Colonic Flora in Humans. Am. J. Clin.

Nutr. 52, 685–88 1990; Fernandes C F & Shahani K M: Anticarcinogenic and Immunological Properties of Dietary Lactobacilli. J. Food Protection 55, 704–710, 1990.
8. Metchnikoff E: The Prolongation of Life: Optimistic Studies. William Heinemann, London 1907, pp. 161–183.
9. Tissier- H: Traitement des infections intestinales per la methode de la flora bacterienne de l'intestin. C. R. Soc. Biol 60, 359–61, 1906.
10. Zhang, Xu-fan etc. Chinese Journal of Epidemiology 3, 277, 1982.
11. Lu, Jin-xin: Chinese Journal of Microecology 2 (1), 15, 1990.
12. Zhang Xu-fan: Chinese Journal of Microecology 2 (1), 15, 1991.
13. Dash S K: Acidophilus: The Friendly Bacteria. Total Health April 1995, 27; Hobbs, Christopher: Foundations of Health, The Liver and Digestion Herbal. Capitola, Calif.: Botannica Press, 92–93, 1992.
14. Bifidobacteria were first described in 1899, and were first recognized as a separate genus in 1974. Tissier M H: La reaction chromophile d'Escherich et *Bacterium Coli*. C. R. Soc. Biol. 51, 943–45, 1899. Modler H W, McKellar R C & Yaguchi M: Bifidobacteria and Bifidogenic Factors. Can. Int. Food Sci. Technol. J. 23, 29–41, 1990.
15. Goldin B R & Gorbach S L: The Effect of Milk and Lactobacillu Feeding on Human Intestinal Bacterial Enzyme Activity. Am. J. Clin. Nutr. 39, 756–61, 1984; Marteau P, Pochart P, Flourie B, Pellier P, Santos L. Desjeux J F & Rambaud J C: Effect of Chronic Ingestion of a Fermented Dairy Product Containing *Lactobacillus acidophilus* and *Bifidobacterium bifidum* on Metabolic Activities on the Colonic Flora in Humans. Am. J. Clin. Nutr. 52, 685–88 1990. Fernandes C F & Shahani K M: Anticarcinogenic and Immunological Properties of Dietary Lactobacilli. J. Food Protection 55, 704–710, 1990.
16. Midolo P D, Lambert J R, Hull R, Luo F and Grayson M L: In vitro Inhibition of *Helicobacter pylori* NCTC 11637 by Organic Acids and Lactic Acid Bacteria. J. Appl. Bacteriol. 79, 475–79, 1995.
17. Bernet M F, Brassart D, Neeser J R and Servin A L: *Lactobacillus acidophilus* LA1 binds to Cultured Human Intestinal Cell Lines and Inhibits Cell Attachment and Cell Invasion by Enterovirulent Bacteria. Gut 35, 483–89 1994; Coconnier M H, Bernet M F, Kerneis S, Chauviere G, Fourniat J and Servin A L: Inhibition of Adhesion of Enteroinvasive Pathogens to Human Intestinal Caco-2 Cells by *Lactobacillus acidophilus* Strain LB Decreases Bacterial Invasion. FEMS Microbiol. Letters 110, 299–306.
18. Apella M C, Gonzalez S N, Nader de Macias M E, Romero N and Oliver G: In vitro Studies on the Inhibition of the Growth of *Shigella sonnei* by *Lactobacillus casei* and *Lactobacillus acidophilus*. J. Appl. Bacteriol. 73, 480–83, 1992.
19. Nader de Macias M E, Romero N C, Apella M C, Gonzalez S N and Oliver G: Prevention of Infections Produced by *Escherichia coli* and *Listeria monocytogenes* by Feeding Milk Fermented with Lactobacilli. J. Food Protection 56, 401–405, 1993.
20. Nader de Macias M E, Apella M C, Romero N C, Gonzalez S N and Oliver G: Inhibition of *Shigella sonnei* by *Lactobacillus casei* and *Lactobacillus acidophilus*. J. Appl. Bacteriol. 73, 407–411, 1992.
21. Fernandes C. et al: Control of Diarrhoea by Lactobacilli. Journal of Applied Nutrition 40, 32–42 1988; Shahani K.: Natural Antibiotic Activity of *L. acidophilus* and Bulgaricus. Cultured Dairy Products Journal 12 (2) 8–11.
22. Klaenhammer T R: Bacteriocins of Lactic Acid Bacteria. Biochimie 70, 337–49, 1988.
23. Malik R K, Kumar N, Nageswara Rao K & Mathur D K: Bacteriocins—Antibacterial Proteins of Lactic Acid Bacteria: A Review. Microbiol. Alim. Nutr. 12, 117–32, 1994; Mital B K & Garg S K: Anticarcinogenic, Hypocholesterolemic, and Antagonistic Activities of *Lactobacillus acidophilus*. Crit. Rev. Microbiol. 21, 175–214, 1995.
24. Dash S K: Acidophilus: The Friendly Bacteria. Total Health Apr., 27, 1995.
25. Goldin B R & Gorbach S L: The Effect of Milk and Lactobacillu Feeding on Human Intestinal Bacterial Enzyme Activity. Am. J. Clin. Nutr. 39, 756–61, 1984; Marteau P, Pochart P, Flourie B, Pellier P, Santos L. Desjeux J F & Rambaud J C: Effect of Chronic Ingestion of a Fermented Dairy Product Containing *Lactobacillus acidophilus* and *Bifidobacterium bifidum* on Metabolic Activities on the Colonic Flora in Humans. Am. J. Clin. Nutr. 52, 685–88, 1990; Fernandes C F & Shahani K M: Anticarcinogenic and Immunological Properties of Dietary Lactobacilli. J. Food Protection 55, 704–710, 1990; Lidbeck A, Overvik E, Rafter J, Nord CE and Gustafsson JA: *Lactobacillus acidophilus* Supplements on Mutagen Excretion in Feces and Urine in Humans. Microbial Ecol. Health Dis. 5, 59–67, 1992.
26. Lee H, Rangavajhyala N, Grandjean C & Shahani K M: Inhibitory Effect of *Lactobacillus acidophilus* on Transformation of Bile Acids by Human Fecal Microflora. Microbiol. Alim. Nutr. 13, 241–47, 1995; Orrhage K, Sillerstrom E, Gustafsson J A, Nord C E and Rafter J: Binding of Mutagenic Heterocyclic Amines by Intestinal and Lactic Acid Bacteria. Mutation Res. 311, 239–48, 1994.

What is claimed is:

1. A microbe composition comprising the bacterial *Bifidobacterium longum* 6-1 (CCTCC Number M 98003), *Lactobacillus acidophilus* YIT 2004 (CCTCC Number M 98004) and *Streptococcus faecalis* YIT 0027 (CCTCC Number M 98005).

2. A microbe composition comprising the bacteria *Bifidobacterium longum* 6-1 (CCTCC Number M 98003), *Lactobacillus acidophilus* YIT 2004 (CCTCC Number M 98004) and *Streptococcus faecalis* YIT 0027 (CCTCC Number M 98005) with a content ratio of colony forming units of 1-5:1-5:1-5.

3. A microbe composition as in claim 1 or 2 further comprising a protective medium wherein said protective medium is 10–20% dried skim milk, 10–20% lactulose, 0.01–0.2% sodium vitamin C, 0.01–2% sodium glutamate, 0.01–2% vitamin E, 6–20% β-cyclodextrin and 6–20% starch.

4. A microbe composition as in claim 1 or 2 wherein said protective medium is 10–20% dried skim milk, 10–20% lactulose, 0.01–0.2% sodium vitamin C, 0.01–2% sodium glutamate, 0.01–2% vitamin E and 6–20% starch.

5. A microbe composition as in claim 1 or 2 wherein said protective medium is 10–20% lactulose, 0.01–0.2% sodium vitamin C, 0.01–2% vitamin E and 6–20% starch.

6. A method for preparing a microbe composition comprising steps of:
   (a) mixing solutions of dried skim milk, glucose and yeast extract;
   (b) sterilizing the mixed solution, then allowing sterilized medium to cool and transferring the medium to three fermentation tanks;

(c) inoculating *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005) with 10% seed respectively into different fementation tanks;

(d) culturing *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005);

(e) separating the bacteria from the medium by centrifugation;

(f) adding a protective medium to the bacteria mud;

(g) Lyophilizing the composition;

(h) Mixing the lyophilized powder with starch and pre-glued starch; and (i) Preparing the lactic acid producing bacteria composition in forms of capsule, tablet or granule.

7. A method for preparing a microbe composition comprising steps of:

(a) mixing solution of 3.5–4% dried skim milk, 1% glucose and 3% yeast extract;

(b) sterilizing the mixed solution in a autoclave at a temperature of 121° C. for 10 minutes, then allowing sterilized medium to three fermentation tanks;

(c) inoculating *Bifidobacterium longum* 6-1 (CCTCC Number M 98003), *Lactobacillus acidophilus* YIT 2004 (CCTCC Number M 98004) and *Sterptococcus faecalis* YIT 0027 (CCTCC Number M 98005) with 10% seed respectively into different fermentation tanks;

(d) culturing *Bifidobacterium longum* 6-1 (CCTCC Number M 98003) at a temperature of 37–38° C., a pressure of 0.3–0.6 kg/cm (inner) under anaerobic and nitrogenous conditions; culturing *Lactobacillus acidophilus* YIT 2004 (CCTCC Number M 98004) and *Sterptococcus faecalis* YIT 0027 (CCTCC Number M 98005) at the same temperature and pressure but with sterile gas;

(e) separating the bacteria from the medium by centrifugation at 20,000 rpm;

(f) adding protective medium to the bacteria mud;

(g) lyophilizing the composition;

(h) mixing the lyophilized powder with starch and pre-glued starch; and (i) preparing the lactic acid producing bacteria composition in forms of capsule, tablet or granule.

8. A method for preparing a microbe composition as in claim 6 or 7, wherein said protective medium comprises 10–20% dried skim milk, 10–20% lactulose, 0.01–0.2% sodium vitamin C, 0.01–2% sodium glutamate, 0.01–2% vitamin E, 6–20% β-cyclodextrin and 6–20% starch.

9. A method for preparing a microbe composition as in claim 6 or 7, wherein said protective medium comprises 10–20% dried skim milk, 10–20% lactulose, 0.01–0.2% sodium vitamin C, 0.01–2% sodium glutamate, 0.01–2% vitamin E and 6–20% starch.

10. A method for preparing a microbe composition as in claim 6 or 7, wherein said protective medium comprises 10–20% lactulose, 0.01–0.2% sodium vitamin C, 0.01–2% vitamin E and 6–20% starch.

11. An oral formulation containing the microbe composition of claim 1 or 2.

12. The oral formulation of claim 11, wherein the formulation is a pill, capsule, tablet, granule or a suspension.

* * * * *

UNITED STATES PATENT AND TRADEMARK OFFICE
CERTIFICATE OF CORRECTION

PATENT NO. : 6,368,591 B2  Page 1 of 1
DATED : April 9, 2002
INVENTOR(S) : Chen et al.

It is certified that error appears in the above-identified patent and that said Letters Patent is hereby corrected as shown below:

Column 13,
Line 32, "kg/cm" should read -- $kg_f/cm^2$ --.

Column 42,
Line 1, "kg/cm" should read -- $kg_f/cm^2$ --.

Signed and Sealed this

Thirty-first Day of January, 2006

JON W. DUDAS
*Director of the United States Patent and Trademark Office*